US006767713B2

(12) United States Patent
Lee et al.

(10) Patent No.: US 6,767,713 B2
(45) Date of Patent: Jul. 27, 2004

(54) PASTEURELLA NEURAMINIDASE DIAGNOSTIC METHODS AND IMMUNOASSAY KIT

(75) Inventors: Margie Lee, Athens, GA (US); Susan Sanchez, Athens, GA (US); Adam Henk, Fort Collins, CO (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/400,122

(22) Filed: Sep. 21, 1999

(65) Prior Publication Data

US 2004/0072153 A1 Apr. 15, 2004

Related U.S. Application Data

(63) Continuation-in-part of application No. 08/951,984, filed on Oct. 15, 1997, now abandoned.

(60) Provisional application No. 60/028,482, filed on Oct. 15, 1996, and provisional application No. 60/028,876, filed on Oct. 16, 1996.

(51) Int. Cl.[7] .................... G01N 33/554; G01N 33/569

(52) U.S. Cl. ........................ 435/7.32; 435/7.1; 435/810

(58) Field of Search ................................ 435/7.32, 810, 435/7.1

(56) References Cited

FOREIGN PATENT DOCUMENTS

WO WO 96/19498 * 6/1996

OTHER PUBLICATIONS

Lederman et al Mol Immund 28(11):1171–1181, 1991.*

Riffkin et al. Gene 167:279–285, 1995.*

Abaza et al. J. Prot. Chem. 11(5):433–444.*

(1988) "Using Synthetic Oligonucleotides as Probes" Current Protocols Unit 6.4.

1997 Annual Meeting of the American Society for Microbiology, Abstract B–497 Lee et al.

Chin–Hsiang Chien et al. (1996) "Site–Directed Mutations of the Catalytic and Conserved Amino Acids of the Neuraminidase Gene, nanH, of Clostridium Perfringens ATCC 10543" *Enzyme and Microbial Technology* 19:267–276.

Drzeniek et al. (1972) "Neuraminidase and N–Acetylneuraminate Pyruvate–Lyase of Pasteurella multocida" *J. of General Microbiology* 72:357–368.

Hoyer et al. (1992) "Cloning, Sequencing and Distribution of the Salmonella typhimurium LT2 Sialidase Gene, nanH, Provides Evidence for Interspecies Gene Transfer" *Mol. Microbiology* 6(7):873–884.

Ifeanyi and Bailie (1992) "Passive Protection of Mice with Antiserum to Neuraminidase from Pasteurella multocida Serotype A:3" *Vet. Research Comm.* 16:97–105.

Lee et al. (1988) "Comparison of Pasteurella multocida serotype 3,4 Isolates from Turkeys with Fowl Cholera" *Avian Diseases* 32:501–508.

Lee et al. (1994) "Invasion of Epithelial Cell Monolayers by Turkey Strains of Pasteurella multocida" *Avian Diseases* 38:72–77.

Roggentin et al. (1993) "The Sialidase Superfamily and its Spread by Horizontal Gene Transfer" *Mol. Microbiology* 9(5):915–921.

Scharmann et al. (1970) "Neuraminidase of Pasteurella multocida" *Infection and Immunity* 1(3):319–320.

Straus et al. (1996) "Characterization of Neuraminidases Produced by Various Serotypes of Pasteurella multocida" *Infection and Immunity* 64(4):1446–1449.

Straus et al. (1993) "Characterization of Neuraminidases Produced by Various Serotypes of Pasteurella haemolytica" *Infection and Immunity* 61(11):4669–4674.

White et al. (1995) "Extracellular Neuraminidase Production by a Pasteurella multocida A:3 Strain Associated with Bovine Pneumonia" *Infection and Immunity* 63(5):1703–1709.

* cited by examiner

*Primary Examiner*—G. R. Ewoldt
(74) *Attorney, Agent, or Firm*—Greenlee Winner and Sullivan PC

(57) ABSTRACT

Provided are *Pasteurella multocida* coding sequences, recombinant DNA molecules, recombinant host cells and methods for making recombinant neuraminidase. Also provided by the present disclosure are immunogenic compositions containing recombinant *P. multocida* neuraminidase and antigenic peptides derived in sequence therefrom and antibodies specific for *P. multocida* neuraminidase as well as immunoassays specific for *P. multocida* neuraminidase, which immunoassays are useful in the detection or diagnosis of *P. multocida* infections and/or carrier states.

4 Claims, 5 Drawing Sheets

PASTEURELLA NEURAMINIDASE DIAGNOSTIC METHODS AND IMMUNOASSAY KIT

CROSS REFERENCE TO RELATED APPLICATIONS

This application claims benefit of and is a continuation-in-part of U.S. patent application Ser. No. 08/951,984, filed Oct. 15, 1997, now abandoned and U.S. Provisional Applications Nos. 60/028,482 and 60/028,876, filed Oct. 15, 1996, and Oct. 16, 1996, respectively.

ACKNOWLEDGEMENT OF FEDERAL RESEARCH SUPPORT

The present invention was made, at least in part, with funding from the National Science Foundation. Accordingly, the United States Government may have certain rights in this invention.

BACKGROUND OF THE INVENTION

The field of this invention is human and/or veterinary vaccines and diagnostics, in particular vaccines comprising *Pasteurella multocida* neuraminidase and/or peptides having amino acid sequences derived therefrom and oligonucleotides useful as specific hybridization probes or specific polymerase chain reaction primers, wherein said vaccines are useful in protecting animals from infection and disease caused by *P. multocida* and wherein the probes or primers are useful in the diagnosis of infection by *Pasteurella multocida* and/or in the detection of pathogenic *P. multocida.*

*Pasteurella multocida* is a gram-negative, oxidase positive rod-shaped bacterium which is a causative agent of human and animal diseases including fowl cholera, shipping fever in cattle, respiratory tract infection, abscesses and systemic infection in various animals. Humans can also be infected by *P. multocida.* This organism often colonizes mucosal tissue, especially in the respiratory system.

Five serotypes based on capsular antigen groupings have been described. Further typing is based on lipopolysaccharide (LPS) structure. Group A strains of *P. multocida* have a capsule which is mainly composed of hyaluronic acid. This capsule contributes to virulence by inhibiting phagocytosis and halogenation of bacterial proteins by the host defense system. The capsule is often lost during subcultures in vitro. Fimbriae are likely to mediate attachment to host tissue early in the infection process. Neuraminidase (sialidase) is an enzyme produced by most pathogenic strains of *P. multocida;* it is believed to contribute to infection and pathogenesis.

Various vaccines are available for *P. multocida* have been developed, with varying degrees of cross-protection for different serotypes and varying levels of effectiveness.

Because *P. multocida* infections pose a threat to the agricultural industry and because such infections result in significant economic losses, because veterinary care is expensive and because *P. multocida* can cause human infections as well, there is a longfelt need in the art for an effective, broad spectrum subunit vaccine to protect humans and animals against *P. multocida.* The present inventors believe that a vaccine comprising *P. multocida* neuraminidase and/or immunogenic peptides derived therefrom fulfill this need. In addition, there is a need for improved methods for diagnosis of *P. multocida* infections.

SUMMARY OF THE INVENTION

An object of the present invention is to provide immunogenic compositions comprising a neuraminidase derived from *P. multocida* or recombinantly expressed from a nucleotide sequence derived from *P. multocida,* which sequence encodes a neuraminidase (or NanH), having a predicted molecular mass of about 44 kDa as a mature protein. In a specifically exemplified *P. multocida* NanH protein, the protein is characterized by an amino acid sequence as given in SEQ ID NO:5, amino acids 1–412.

Whithin the scope of the present invention are methods for protecting animals, including without limitation, sheep, cattle, rabbits, cats, dogs, rodents such as mice, turkeys, chickens and other fowl, and humans, from infection and/or pathology caused at least in partby *P. multocida*, said method comprising the step of administering to said animal or human an immunogenic composition comprising the exemplified neuraminidase or other *P. multocida* neuraminidase with a primary structure similar (more than about 90% amino acid sequence identity) to the exemplified neuraminidase, and/or one or more peptides derived from one or more of the foregoing proteins or having amino acid sequence(s) taken from the amino acid sequence(s) of one or more of the foregoing proteins, wherein said peptide or protein, when used in an immunogenic composition in an animal, including a human, confers protection against infection by and/disease caused at least in part by *P. multocida.* As specifically exemplified, immunogenic peptides include VVMFDLRWKTASDQNRIDPG (SEQ ID NO: 1); MHGTWAAGTQNWYRDRLSY (SEQ ID NO:2); and HKHQVAIIRPGSGNAGAGYSSLAY (SEQ ID NO:3).

Substantially pure recombinant 47.4 to 50 kDa neuraminidase can be prepared after expression of a nucleotide sequence encoding neuraminidase in a heterologous host cell using the methods disclosed herein or from *P. multocida* outer membranes. Specifically exemplified partial neuraminidase amino acid sequences are given in Table 2.

As specifically exemplified herein, the nucleotide sequence encoding a mature *P. multocida* neuraminidase is given in SEQ ID NO:4, nucleotides 251 through 1486, exclusive of the signal peptide and stop codon. The complete coding sequence, including the N-terminal signal peptide of 21 amino acids is given in SEQ ID NO:4 from nucleotide 188 through 1486, exclusive of the stop codon. All synonymous coding sequences are within the scope of the present invention. The skilled artisan will understand that the coding or amino acid sequence of the exemplified neuraminidase protein can be used to identify and isolate additional, non-exemplified nucleotide sequences which will encode a functional protein of the same amino acid sequence as given in SEQ ID NO:5 from amino acid 1–412 or as given in SEQ ID NO:5 from −21 to 412 or an amino acid sequence of greater than 90% identity to either of the foregoing and having neuraminidase activity. Additional, partial neuraminidase coding sequences which identify other *P. multocida* sequences are given in Table 1 herein. The skilled artisan understands that it may be desirable to express the neuraminidase as a secreted protein; if so, it is known how to modify the exemplified coding sequence for the "mature" neuraminidase, by adding a nucleotide sequence encoding a signal peptide appropriate to the host in which the sequence is expressed. The skilled artisan understands that it may be desirable to express the neuraminidase as a secreted protein; if so, it is known how to modify the exemplified coding sequence for the "mature" neuraminidase, by adding a nucleotide sequence encoding a signal peptide appropriate to the host in which the sequence is expressed. When it is desired that the sequence encoding a neuraminidase protein be expressed, then the skilled artisan will operably link transcription and translational control regulatory sequences to the coding sequences, with the choice of the regulatory sequences being determined by the hose in which the coding sequence is to be expressed. With respect to a recombinant DNA molecule carrying a neuraminidase coding sequence, the skilled artisan will chose a vector (such as a plasmid or a viral vector) can be introduced into and which can replicate in the host cell. The host cell can be a bacterium, preferably *Escherichia coli,* or a yeast or a mammalian cell. Recombinant vectors carrying NanH coding sequences and recombinant host cells comprising same are also within the scope of the present invention.

The present invention also provides for fusion polypeptides comprising at least one epitope of a *P. multocida* neuraminidase, which is capable of providing full or partial protective immunity to an animal (or human) vaccinated with an effective amount of said fusion protein in an immunogenic composition. Homologous polypeptides may be fusions between two or more neuraminidase sequences. Likewise, heterologous fusions may be constructed which would exhibit a combination of properties or activities of the proteins from which they are derived. Fusion partners include, but are not limited to, a nontoxic fragment of cholera toxin, immunoglobulins, ubiquitin, bacterial β-galactosidase, TrpE, protein A, β-lactamase, alpha amylase, alcohol Dehydrogenase and yeast alpha mating factor [Godowski et al. (1988) *Science* 241:812–816]. Fusion proteins will typically be made by recombinant methods but may be chemically synthesized. Preferably, the NanH portion of such a fusion protein comprises the region encoded downstream of about nucleotide 1500 in SEQ ID NO:4.

Compositions and immunogenic preparations including but not limited to vaccines, comprising at least one *P. multocida* neuraminidase and/or a peptide derived therefrom, and a suitable carrier therefor are provide; preferably such immunogenic compositions further comprise an adjuvant. Such immunogenic compositions and vaccines are useful, for example, in immunizing an animal, including a human, against infection by and/or disease caused by *P. multocida.* The vaccine preparations comprise an immunogenic amount of a Pasteurella neuraminidase or an immunogenic peptide fragment or synthetic peptide of same. Such vaccines may comprise one or more neuraminidases in combination with another protein or other immunogen. By "immunogenic amount" is meant an amount capable of eliciting the production of antibodies directed against one or more *P. multocida* neuraminidase (or one or more peptides whose amino acid sequence is derived from the foregoing protein) in an individual or animal to which the vaccine has been administered.

It is a further object of the present invention to provide primers and PCR-based methods for the diagnosis of a *P. multocida* infection or the detection of *P. multocida* cells in a sample, such as a biological sample including, but not limited to, respiratory system exudate, infected tissue, abscess-derived material, stool sample or tissue from a reservoir of infection such as the mouse. A sample may be taken from a suspected infected animal, for example in suspected outbreak of fowl cholera in chickens or turkeys, suspected shipping fever in sheep or cattle, a diseased rabbit, a cat or dog with an abscess or from a human potentially infected with *P. multocida.* Forward primer 5'-GCTTTGAATGGCAGTTTATATGTG-3' (SEQ ID NO:6) and reverse primer 5'-TGAAGGAGCCGCTGTAGTCG-3' (SEQ ID NO:7) (derived from the *P. multocida* R1913 nanH gene) are used to amplify a fragment of about 511 bp of a *P. multocida* nanH gene. The skilled artisan understands that alternative primers can also be designed using the nucleotide sequence information provided herein, taken with information readily accessible and well known to the art.

Additionally, the present invention provides for immunoassays for detection and/or diagnosis of *Pasteurella multocida* infection (or carrier state) in animals of humans. Such immunoassays contain antibodies specific for a neuraminidase of the present invention, where the neuraminidase is encoded by a nucleotide sequence having at least about 90% homology to SEQ ID NO:4, amino acids 1–412 and where the *P. multocida* neuraminidase in an infected or carrier animal has antigenic determinants in common with the specifically identified neuraminidase.

DETAILED DESCRIPTION OF THE INVENTION

Figure 1:
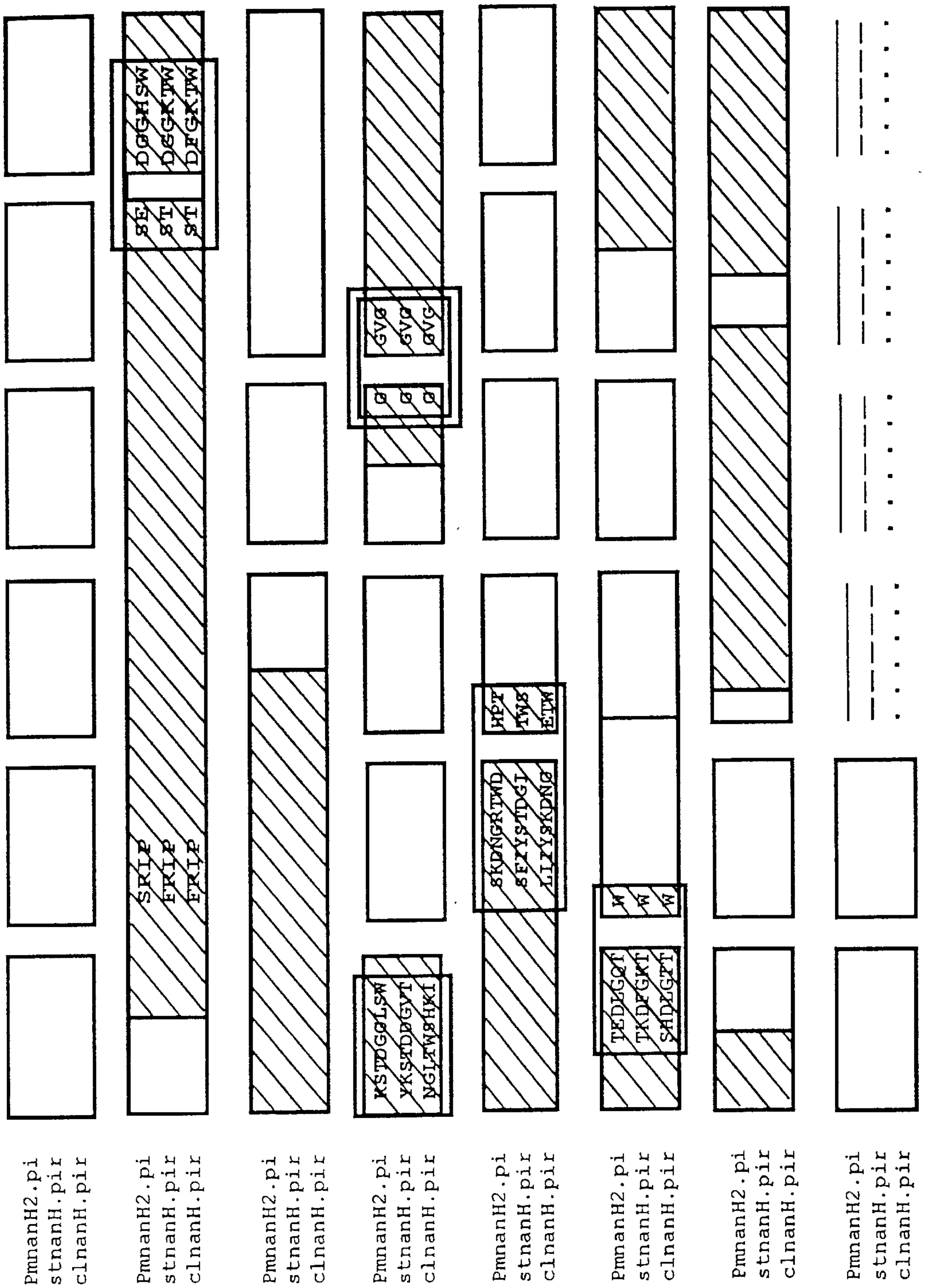
FIG. 1 provides the amino acid sequence alignment of *P. multocida* (pmnanH2), *S. typhimurium* (stnanH), and *C. perfringens* (clnanH) neuraminidases. Cross-hatched blocks indicate regions of similarity, open blocks denote regions of dissimilarity. The asparagine repeats are contained within boxes, the "FRIP (SEQ ID NO:8)" box is marked is noted, and the box within the double line shows the region of the invariant glycine residue. Sequence identifiers are as follows: SRIP, SEQ ID NO:12, FRIP, SEQ ID NO:8, SEDGGHSW, amino acids 87–95 of SEQ ID NO:5, STDGGKTW, SEQ ID NO:13, STDFGKTW, SEQ ID NO:18, KSTDGGLSW, amino acids 160–168 of SEQ ID NO:5, YKSTDDGVT, SEQ ID NO:14, NGLTWSHKI, SEQ ID NO:19, GGVG, SEQ ID NO:15, SKDNGRTWDHPT, amino acids 231–242 of SEQ ID NO:5, SFIYSTDGITWS, SEQ ID NO: 16, LIIYSKDNGETW, SEQ ID NO:20, TEDLGQT, amino acids 283–289 of SEQ ID NO:5, TKDFGKTW, SEQ ID NO:17, and SHDLGTTW, SEQ ID NO:21.
Figure 2:
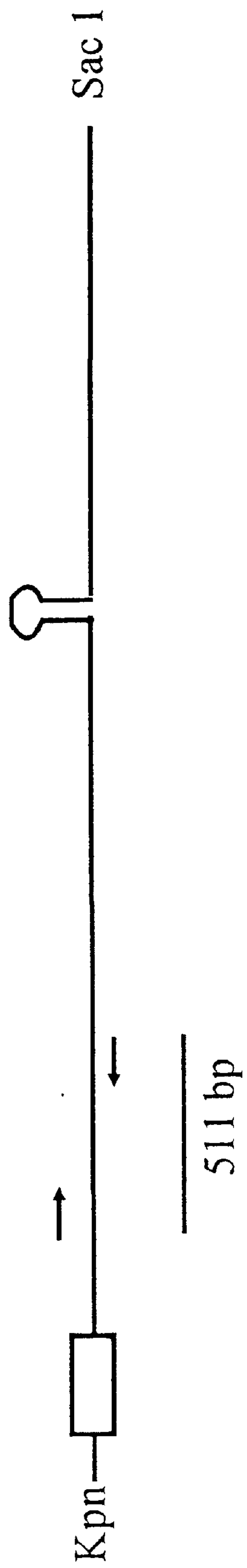
FIG. 2 is a schematic of the nanH gene of *P. multocida.* The arrows show the positioning of the primers which produced the internal amplification producti of 511 bp by PCR.
Figure 3:
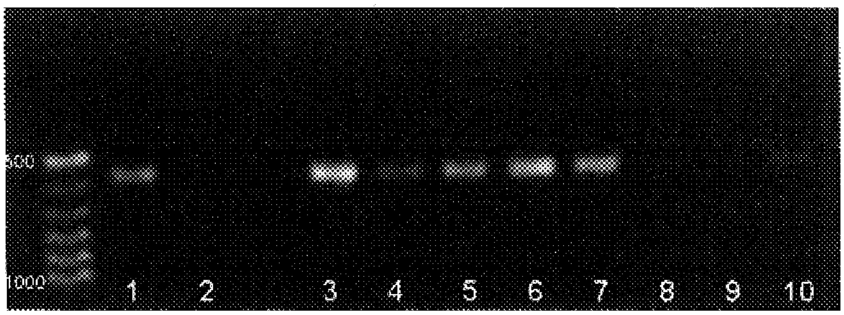
FIG. 3 is a photograph of *P. multocida* nanH-specific PCR products separated on a 1% agarose gel: Lane 1, isolate R1913; lane 2, *E. coli;* lane 3, CU; lanes 4–10 contain DNA from the field isolates 6797C, 241, 1796, 162, 67-2, 2120 and 2667, respectively. Molecular weight markers (bp) are located to the left of lane 1.
Figure 4:
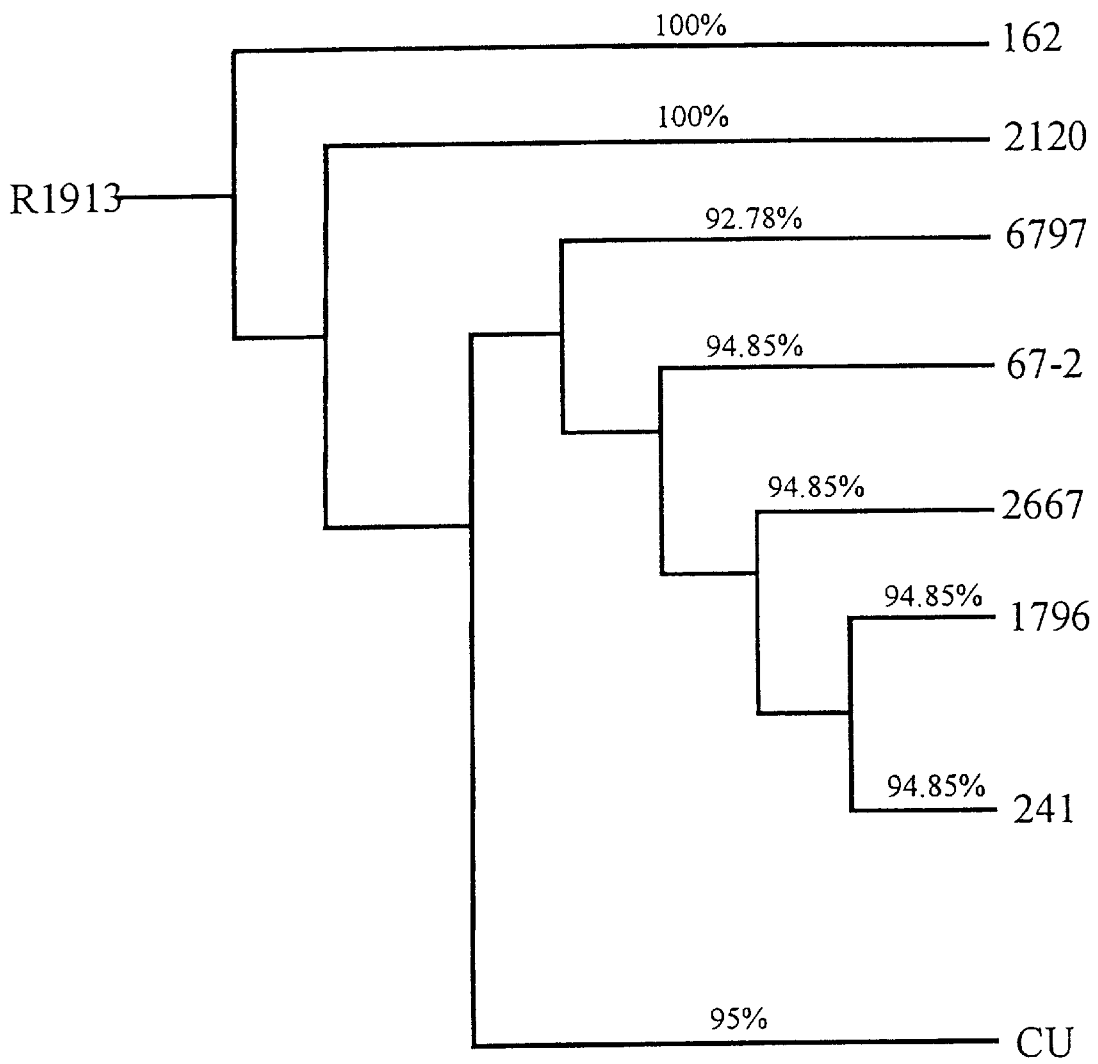
FIG. 4 is a phylogenetic tree constructed using the PHYLIP algorithm and sequence alignments for the amplification product sequences.

Abbreviations used herein for amino acids are standard in the art: X or Xaa represents an amino acid residue that has not yet been identified but may be any amino acid residue including but not limited to phosphorylated tyrosine, threonine or serine, as well as cysteine or a glycosylated amino acid residue. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine.

Neuraminidases (sialidases) are enzymes which remove sialic acid from glycoproteins, glycolipid compounds, or colominic acids by cleaving the alpha-ketosidic linkages. It is hypothesized that neuraminidase contributes to the virulence of some pathogenic organisms, especially those that inhabit mucosal surfaces [Corfield, T. (1992) *Glycobiology* 2:509–521]. Drzeniek et al. (1972) *J. Gen. Microbiol.* 72:357–368 found neuraminidase activity in bacterial isolates that belong to the order Pseudomonadales and Eubacteriales. Neuraminidases isolated from Clostridium, *Vibrio cholerae* [Roggentin et al. (1993) *Mol. Microbiol.* 9(5):915–921], and *Salmonella typhimurium* [Hoyer et al. (1992) *Mol. Microbiol.* 6(7):873–884] have been extensively studied. All isolates of *Pasteurella multocida* and 3 out of 5 *P. haemolytica* also have neuraminidase activity [Drzeniek et al. (1972) *J. Gen. Microbiol.* 72:357–368; Scharmann et al. (1970) *Infect. Immun.* 1:319–320]. All bacterial neuraminidases which have been studied demonstrate 20–50% similarity at the amino acid level and a common motif, the asparagine box (-S-X-D-X-G-T-W-) (SEQ ID NO:9), is repeated 4–5 times [Hoyer et al. (1992) *Mol. Microbiol.* 6(7):873–884]. The bacterial neuraminidases are divided into two groups depending on size. Most of the clostridial and the Salmonella neuraminidases are less that 47.4 to 50 kDa in size while the neuraminidase of *C. sordelli* and *V cholerae* are greater than 100 kDa [Hoyer et al. (1992) *Mol. Microbiol.* 6(7):873–884]. White et al. (1995) *Infect. Immun.* 63(5): 1703–1709 and Straus et al. (1993) *Infect. Immun.* 61:4669–4674 report that the Pasteurella neuraminidase is in excess of 250 kDa. However, Ifeanyi and Bailie (1992) *Vet. Res. Common.* 16:97–105 reported that the enzyme is 36 kDa in size. The objective of this study was to study the neuraminidase gene of *P. multocida* by sequence analysis.

*E. coli* transformed with the 3.2 kb fragment containing nanH produced neuraminidase activity as did the wild type *P. multocida.* DNA sequencing revealed that nanH resides on an 1300 bp fragment and encodes a protein of approximately 47.4 kDa. The predicted amino acid sequence contains a hydrophobic signal sequence of 21 amino acids which, when cleaved, results in a 43.8 kDa product. Because expression of the enzyme was toxic to *E. coli,* its molecular weight could not be determined from the original constructs. The His construct which contains 16 AA of signal sequence does not produce stable neuraminidase in *E. coli* (degradation problems) but a new one was made without the signal sequence. This His-tagged recombinant protein lacks the signal sequence and is 44 kDa in size. This protein was produced by cloning the ORF using PCR with primers that contained a restriction endonuclease site [forward 5'AAGACCAGATCTATGCATGAAAATTTAACT 3' (SEQ ID NO: 10) which contains a BamHI site and reverse 5'AGTTTTCGAATTAACCCCATTCTGTG 3' (SEQ ID NO:11)]. The PCR product (1500 bp) was first cloned into pGEM-T (Promega, Madison, Wis.) then subcloned using BamHI, SacI into pQE32. A 1.7 kb fragment was subcloned in pQE32 in order to produce an amino-terminal histidine-tagged protein, which was then purified by nickel-affinity chromatography. The fusion was confirmed to be in frame by DNA sequencing. This neuraminidase lacked 5 amino-terminal amino acids of the native enzyme, was produced intracellularly, and migrated in the 40,000 molecular weight range in SDS-PAGE. The complete amino acid sequence of the exemplified mature native neuraminidase is given in SEQ ID NO:5; the predicted protein is preceded by an N-terminal signal peptide of 21 amino acids (−21 to −1 in SEQ ID NO:5). In nature, this protein is produced by *P. multocida* strain R1913; it can be purified from the cell surface. The exemplified protein can also be produced recombinantly in suitable host cells genetically engineered to contain and express the exemplified, a synonymous, or a substantially similar coding sequence. As specifically exemplified herein, the coding sequence of mature nanH gene product of *P. multocida* is given in SEQ ID NO:4, from nucleotide 251 through the stop codon ending at nucleotide 1489. The signal peptide is encoded at nucleotides 188 through 250. All synonymous codings are encompassed within the present invention, as are coding sequences for a neuraminidase having at least about 90% nucleotide sequence homology to the exemplified sequence.

The predicted amino acid sequence contains a hydrophobic signal sequence of 21 amino acids and 4 asparagine boxes. Structure predictions suggest that the protein is primarily beta-sheet, which would produce a beta-propeller protein, the tertiary structure of neuraminidases (see the NIH Molecules 'R Us repository on the Internet). Like other bacterial neuraminidases, the *P. multocida* NanH is hydrophilic. Aligning the amino acid sequences of the *S. typhimurium, C. perfringens* and *P. multocida* NanH protein reveals some amino acid sequence relatedness among these enzymes (FIG. 1).

While the *P. multocida* NanH amino acid sequence has some similarity to the amino acid sequences of other bacterial neuraminidases, the exemplified DNA sequence does not exhibit significant homology to any other gene sequence deposited in GenBank. The open reading frame encodes a protein of approximately 47.4 to 50 kDa, including a signal peptide. It is possible that the discrepancy among published reports results from the isolation of aggregates or degradation products of the protein which may retain some enzymatic activity in those previous reports. Without wishing to be bound by theory, it is also possible that *P. multocida* produces more than one enzyme with neuraminidase activity, as has been seen in some clostridial species [Roggentin et al. (1993) *Mol. Microbiol.* 9(5):915–921].

The predicted amino acid sequence of the *P. multocida* NanH contains four asparagine repeats. Other researchers have shown that the regions containing the asparagine repeats are conserved among neuraminidases isolated from many species of organisms [Roggentin et al. (1993) *Mol. Microbiol.* 9(5):915–921]. This motif is believed to be involved in creating the active site of the enzyme and is present in 4–5 copies in every bacterial neuraminidase which has been studied. The *P. multocida* NanH also contains a "FRIP" (SEQ ID NO:8) box sequence at amino acids 51–54 and a glycine-enriched region at amino acids 197–202 in SEQ ID NO:5, both of which are common to bacterial neuraminidases. There are also four "asparagine repeats" in the specifically exemplified *P. multocida* R1913 NanH: SEDGGHSW at amino acids 87–95, STDGGHSW at amino acids 161–168, SKDNGRTW at amino acids 231–238 and TEDLEQTW at amino acids 283–290, all in SEQ ID NO:5. The invariant glycine residues are present within the glycine-rich region at amino acids 197–202 in SEQ ID NO:5. See also FIG. 1, pmnanH2.pi sequences.

The presence of an amino-terminal signal peptide sequence of 19 amino acids suggests that the enzyme is membrane bound, although no transmembrane spanning regions were predicted. The carboxy-terminus is predicted to form an elongated alpha helix whose amino acid sequence demonstrates similarity to several adhesion proteins. It is possible that the *P. multocida* neuraminidase has two domains: one enzymatic and one involved in bacterial attachment. The *V. cholerae* NanH contains two domains, one of which is structurally similar to lectins [Roggentin et al. (1993) *Mol. Microbiol.* 9(5):915–921].

The skilled artisan recognizes that other *P. multocida* strains can have coding sequences for a protein with the distinguishing characteristics of a neuraminidase; those coding sequences may be identical to or synonymous with the exemplified coding sequence, or there may be some variation(s) in the encoded amino acid sequence. A neuraminidase coding sequence from a *P. multocida* strain other than R1913 can be identified by, e.g. hybridization to a polynucleotide or an oligonucleotide having the whole or a portion of the exemplified coding sequence for mature neuraminidase, under stringency conditions appropriate to detect a sequence of at least 70% homology. The skilled artisan understands the hybridization conditions or PCR conditions necessary for detection of such a sequence in an organism where the G+C content is about 40%. Tables 1–2 compare *P. multocida* neuraminidase coding and amino acid sequences over a stretch of about 511 bp and 170 amino acids.

Without wishing to be bound by any particular theory, it is believed that the coding sequence of the 47.4 to 50 kDa neuraminidase extends from an ATG beginning at nucleotide 188 and extending through a translation stop codon ending at nucleotide 1489 in SEQ ID NO:4. Without wishing to be bound by any particular theory, it is believed that a signal peptide of 21 amino acids precedes the active neuraminidase.

SEQ ID NO:4 represents a neuraminidase coding sequence from *P. multocida* strain R1913. However, it is understood that there will be some variations in the amino acid sequences and encoding nucleic acid sequences for neuraminidase from different *P. multocida* strains. The ordinary skilled artisan can readily identify and isolate neuraminidase sequences from other strains where there is at least 70% homology, preferably about 80% and more preferably about 90% homology to the specifically exemplified sequences herein using the sequences provided herein taken with what is well known to the art, e.g., polymerase chain reaction and/or nucleic acid hybridization techniques and taking into account the G+C content of about 40%. Also within the scope of the present invention are *P. multocida* neuraminidases where the neuraminidase (or proteolytic component) has at least about 90% amino acid sequence identity with the amino acid sequence exemplified herein.

It is also understood by the skilled artisan that there can be limited numbers of amino acid substitutions in a protein without significantly affecting function, and that nonexemplified neuraminidases can have some amino acid sequence divergence from the exemplified amino acid sequence. Such naturally occurring variants can be identified, e.g., by hybridization to the exemplified (mature) nanH coding sequence (or a portion thereof capable of specific hybridization to neuraminidase sequences) under conditions appropriate to detect at least about 70% nucleotide sequence homology, preferably about 80%, more preferably about 90% or 95–100% sequence homology. Preferably the encoded neuraminidase has at least about 90% amino acid sequence identity to an exemplified neuraminidase amino acid sequence.

It is well known in the biological arts that certain amino acid substitutions can be made in protein sequences without affecting the function of the protein. Generally, conservative amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure,* Volume 5, Supplement 3, Chapter 22, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Nine field isolates of *P. multocida* were obtained from fowl cholera outbreaks in Georgia and South Carolina. They were characterized as Serotype 3 or 3×4 by the Poultry Diagnostic Research Center at the University of Georgia. Serotype reference strains and the Clemson University serotype 3×4 vaccine strain CU were also tested. All isolates showed neuraminidase activity in the 2'-(4-methylumbelliferyl)-α-D-N-acetylneuraminic acid assay using whole cells.

Southern hybridization analysis (dot blots) showed that all isolates contained nanH sequences homologous to the exemplified nanH sequence disclosed herein. PCR reactions using the exemplified nanH-specific primers and analysis of the amplification products demonstrated that all isolates had a sequence of about 511 bp, as did the nanH specifically exemplified herein (see Table 5).

When the amplification products from PCR carried out on the 9 Serotype 3 isolates were sequenced and the sequences were compared and aligned (see Tables 1 and 2 hereinbelow), it was determined that there is significant sequence conservation in this region of the nanH genes. Additional sequence alignments based on PCR results were determined. Based on a phylogenetic tree constructed using the amplimer sequences, two isolates (162 and 2120) show 100% homology with R1913 nanH while the remaining isolates show 94.8% homology and CU shows 95% homology (Table 3). The field isolate 6797C exhibits only 92.7% homology which, without wishing to be bound by theory, is believed to be because it is a Serotype 3 isolate. Deduced amino acid sequence alignments show that NanH amino acid sequences are highly conserved despite some DNA sequence divergence. There are 3 asparagine repeat motifs (S-X-D-X-G-T-W) (SEQ ID NO:9), characteristic of bacterial neuraminidases. The limited sequence variation shows that these regions are conserved as is an invariant glycine.

PCR using the nanH specific primers described herein resulted in products of the expected size from all 3,4 isolates and all serotypes except 1 and 14 (Table 3). The PCR products were sequenced to confirm their identities. All of the products from serotypes 4–13, 15–16 and 3,4 demonstrated at least 90% homology with the corresponding cloned nanH. The PCR products from serotypes 4, 5, 11, 15, and 16 contained an identical 12 bp insert corresponding to 4 additional amino acids in one of the extra propeller loop regions of the enzyme.

Examination of the predicted secondary structures for the R1913, CU and 6797C neuraminidases reveals that only the amino acid differences in the CU neuraminidase resulted in changes in the predicted frequency of helix formation. Even though 6797C nanH is least homologous to R1913 at the DNA sequence level, its NanH predicted secondary structure is very similar. The predicted structures of the neuraminidases of other isolates were predicted to be essentially identical to the predicted structure of the R1913 NanH protein.

Additional isolates of *P. multocida* were subjected to PCR analysis of nanH sequences using the primers disclosed hereinabove. Isolates of serotypes 3,4,5 and 7–16 each gave the expected amplification product of about 511 pb (by agarose gel electrophoresis). Serotype 6 produced an amplification product using the primers disclosed herein. No serotype 2 isolates were tested. The serotype 1 isolate examined yielded a PCR amplification product of about 1 kb. Thus, most field isolates of *P. multocida* harbor a nanH with sequence substantially similar to that specifically exemplified herein, as tested according to Example 3. Therefore, PCR detection and/or diagnostic methods using the primer sequences disclosed herein are appropriate for detection of pathogenic *P. multocida* and the NanH protein and related peptides are useful in protective broad spectrum (i.e., not serotype-specific) vaccines effective for protection of animals and humans from infection by and/or disease caused by *P. multocida.* Moreover, the PCR method of the present invention with the specifically exemplified primers can be applied to the detection of most other serotypes of *P. multocida* as well. Only serotypes 1 and 14 did not give a positive result (see Table 5).

A polynucleotide or fragment thereof is “substantially homologous” (or “substantially similar”) to another polynucleotide if, when optimally aligned (with appropriate nucleotide insertions or deletions) with another polynucleotide, there is nucleotide sequence identity for approximately 60% of the nucleotide bases, usually approximately 70%, more usually about 80%, preferably about 90%, and more preferably about 95% to 100% of the nucleotide bases.

Alternatively, substantial homology (or similarity) exists when a polynucleotide or fragment thereof will hybridize to another under polynucleotide under selective hybridization conditions. Selectivity of hybridization exists under hybridization conditions which allow one to distinguish the target polynucleotide of interest from other polynucleotides. Typically, selective hybridization will occur when there is approximately 55% similarity over a stretch of about 14 nucleotides, preferably approximately 65%, more preferably approximately 75%, and most preferably approximately 90%. See Kanehisa (1984) *Nucl. Acids Res.* 12:203–213. The length of homology comparison, as described, may be over longer stretches, and in certain embodiments will often be over a stretch of about 17 to 20 nucleotides, and preferably about 36 or more nucleotides. The hybridization of polynucleotides is affected by such conditions as salt concentration, temperature, or organic solvents, in addition to the base composition, length of the complementary strands, and the number of nucleotide base mismatches between the hybridizing polynucleotides, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1 M, typically less than 500 mM, and preferably less than 200 mM. However, the combination of parameters is much more important than the measure of any single parameter [Wetmur and Davidson (1968) *J. Mol. Biol.* 31:349–370].

An “isolated” or “substantially pure” polynucleotide is a polynucleotide which is substantially separated from other polynucleotide sequences which naturally accompany a native neuraminidase (nanH sequence). The term embraces a polynucleotide sequence which has been removed from its naturally occurring environment, and includes recombinant or cloned DNA isolates, chemically synthesized analogues and analogues biologically synthesized by heterologous systems.

A polynucleotide is said to “encode” a polypeptide if, in its native state or when manipulated by methods known to those skilled in the art, it can be transcribed and/or translated to produce the polypeptide of a fragment thereof. The antisense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term “non-naturally occurring” or “recombinant” nucleic acid molecule refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other neuraminidase coding sequences. Probes comprising synthetic oligonucleotides or other polynucleotides may be derived from naturally occurring or recombinant single or double stranded nucleic acids or be chemically synthesized, and they may be used in polymerase chain reactions as well as in hybridizations. Polynucleotide probes may be labeled by any of the methods known in the art, e.g., random hexamer labeling, nick translation, or the Klenow fill-in reaction. Oligonucleotides or polynucleotide primers useful in PCR are readily understood and accessible to the skilled artisan using the sequence information provided herein taken with what is well known to the art. Particularly preferred oligonucleotides for use as primers in PCR are forward primer 5'-GCTTTGAATGGCAGTTTATATGTG-3' (SEQ ID NO:6) and reverse primer 5'-TGAAGGAGCCGCTGTAGTCG-3' (SEQ ID NO:7).

Large amounts of the polynucleotides may be produced by replication in a suitable host cell. Natural or synthetic DNA fragments coding for a neuraminidase or a fragment thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli,* although other prokaryotes, such as *Bacillus subtilis* or Pseudomonas may also be used. Mammalian or other eukaryotic host cells include yeast, filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.* 22:1859–1862 or the triester method according to Matteuci et al. (1981) *J. Am. Chem. Soc.* 103:3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1992) *Current Protocols in Molecular Biology,* Greene Publishing and Wiley Interscience, New York,; and Metzger et al. (1988) *Nature* 334:31–36. Many useful vectors for expression in bacteria, yeast, mammalian, insect, plant or other cells are well known in the art and may be obtained such vendors as Stratagene, New England Biolabs, Promega Biotech, and others. In addition, the construct may be joined to an amplifiable gene (e.g., DHFR) so that multiple copies of the gene may be made. For appropriate enhancer -and other expression control sequences, see also *Enhancers and Eukaryotic Gene Expression,* Cold Spring Harbor Press, NY (1983). While such expression vectors may replicate autonomously, they may less preferably replicate by being inserted into the genome of the host cell.

Expression and cloning vectors desirably contains a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The recombinant vectors containing the NanH coding sequence of interest can be introduced (transformed, transfected) into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral or retroviral genome). The choice of such means will often depend on the host cell. Large quantities of the polynucleotides and polypeptides of the present invention may be prepared by transforming suitable prokaryotic or eukaryotic host cells with neuraminidase-encoding polynucleotides of the present invention in compatible vectors or other expression vehicles and culturing such transformed host cells under conditions suitable to attain expression of the neuraminidase-encoding sequence. The NanH protein may then be recovered from the host cell and purified.

It is preferred that NanH for use in immunogenic compositions, including vaccines, is not associated with or accompanied by lipopolysaccharide of a virulent strain of *P. multocida.* Without wishing to be bound by theory, it is believed that such LPS is immunodominant, with the result that resulting immunity is predominantly directed to that LPS and is LPS-specific where the LPS was present in the immunogenic compositions.

The coding sequence for the "mature" form of the 47.4 to 50 kDa neuraminidase of *P. multocida* is expressed after PCR site-directed mutagenesis and cloning into an expression vector suitable for use in *E. coli,* for example, or in another desired host cell. Alternatively, a NanH expression vector can be introduced into a nonvirulent *P. multocida* for use in a live, attenuated vaccine which could be orally administered in food or water, for example to flocks of chickens or turkeys to prevent fowl cholera. Oral vaccines are desirable where the numbers (or temperament) of animals to be vaccinated makes individual injections impractical. Exemplary expression vectors for *E. coli* and other host cells are given, for example in Sambrook et al. (1989), vide infra, and in Pouwels et al. (Eds.) (1986) *Cloning Vectors,* Elsevier Science Publishers, Amsterdam, the Netherlands.

In order to eliminate 5' untranslated and signal sequences at the 5' side of the coding sequence, a combination of restriction endonuclease cutting and site-directed mutagenesis via PCR using an oligonucleotide containing a desired restriction site for cloning (one not present in coding sequence), a ribosome binding site, an translation initiation codon (ATG) and the codons for the first amino acids of a mature neuraminidase. The oligonucleotide for site-directed mutagenesis at the 3' end of the coding sequence for mature NanH includes nucleotides encoding the carboxyterminal amino acids of the mature neuraminidase, a translation termination codon (TAA, TGA or TAG), and a second suitable restriction endonuclease recognition site not present in the remainder of the DNA sequence to be inserted into the expression vector. Site-directed mutagenesis strategy is described, for example, Boone et al. (1990) *Proc. Natl. Acad. Sci. USA* 87:2800–2804, with modifications for use with PCR as readily understood by the skilled artisan.

The skilled artisan understands that it may be advantageous to modify the exemplified nanH coding sequence, which is about 40% G+C, for improved expression in a particular recombinant host cell. Such modifications, which can be carried out without the expense of undue experimentation using the present disclosure taken with knowledge and techniques readily accessible in the art, can include adapting codon usage so that the modified nanH coding sequence has codon usage substantially like that known for the target host cell. Such modifications can be effected by chemical synthesis of a coding sequence synonymous with the exemplified coding sequence or by oligonucleotide site-directed mutagenesis of selected portions of the coding sequence.

Immunogenic peptides and oligopeptides having amino acid sequences derived from the exemplified neuraminidase protein can be chemically synthesized using art-known techniques, for example, using those described in Stewart et al. (1984) *Solid Phase Peptide Synthesis,* Pierce Chemical Co., Rockford, Ill., or a by automated synthesis, using for example, commercially available equipment. Multiple antigen peptides and synthesis methods are described in, e.g., Tam, J. P. (1988) *Proc. Natl. Acad. Sci. USA* 85:5409–5413, Posnett et al. (1988) *J. Biol. Chem.* 263:1719–1725; Briand et al. (1992) J. Immunol. Meth. 156:255–265.

In another embodiment, polyclonal and/or monoclonal antibodies capable of specifically binding to the *P. multocida* NanH or fragments thereof are provided. The term antibody is used to refer both to a homogenous molecular entity, or a mixture such as a serum product made up of a plurality of different molecular entities. Monoclonal or polyclonal antibodies specifically reacting with the exemplified neuraminidase may be made by methods known in the art. See, e.g., Harlow and Lane (1988) *Antibodies: A Laboratory Manual,* Cold Spring Harbor Laboratories; Goding (1986) *Monoclonal Antibodies: Principles and Practice,* 2d ed., Academic Press, New York; and Ausubel et al. (1987) supra. Also, recombinant immunoglobulins may be produced by methods known in the art, including but not limited to the methods described in U.S. Pat. No. 4,816,567. Monoclonal antibodies with affinities of $10^8$ $M^{-1}$, preferably $10^9$ to $10^{10}$ or more are preferred.

Antibodies specific for the *P. multocida* neuraminidase may be useful, for example, as probes for screening DNA expression libraries or for detecting the presence of *P. multocida* and/or the exemplified neuraminidase in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States Patents describing the use of such labels include, but are not limited to, Nos. 3,817,837; 3,850,752; 3,939,350; 3,996,345; 4,277,437; 4,275,149; and 4,366,241.

Antibodies specific for the exemplified neuraminidase and capable of inhibiting its enzymatic activity are useful in treating animals, including man, susceptible to or suffering from infection by *P. multocida.* Such antibodies can be obtained by the methods described above and subsequently screening the antibodies for their ability to inhibit neuraminidase activity.

Antibodies specific for the *P. multocida* neuraminidase are also useful in the diagnosis or detection of *P. multocida* infection in animals, including acute infections as well as subacute infections in individual animals or humans or within an animal population such as a laboratory animal colony, fowl farm, or a commercial animal production facility. A diagnostic method based on one or more antibodies specific for NanH or a peptide specific thereto can be used in kits for the detection and/or diagnosis of *P. multocida* biological samples for animals (or humans). Such antibodies can be incorporated, for example, in kits for ELISA (enzyme-linked immunosorbent assays), optical immunoassays, or any other amplified or unamplified immunoassay known to the art.

The present inventors have developed an ELISA assay dependent on the neuraminidase of the present invention for use in the diagnosis of *P. multicoda* infection (or carrier state) in humans or animals (See Example 6 hereinbelow). Previous culture methods for diagnosis of *P. multocida* infections have not been as reliable as needed; it has been reported that up to about 30% of *P. multocida*-infected animals have failed to yield positive results with single bacterial culture attempts. In addition, prior art immunological assays have been dependent on whole cell or uncharacterized protein extracts. Because *P. multocida* lipopolysaccharide (LPS) appears often to be immunodominant and because results depend on the particular LPS serotype of the infecting strain as compared to that used in the assay reagents, those prior art assays also have not been as reliable as medical and veterinary practitioners require. Patient (animal or human) samples for testing can include, without limitation, saliva, swabs of mucosal or dental surfaces, lesion scrapings, sputum, serum, blood, biopsy material or tissue samples.

Pet rabbits, patients in five veterinary practices to which free testing of the present ELISA was offered, were the subject of experiments described herein. 55 serum samples and 38 swabs (from lesions or from nasal mucosa) were obtained and tested using the present ELISA and conventional culture methods and polymerase chain reaction (PCR) assays. The animals which were positive by culture or PCR were also positive in the ELISA. The results are summarized in Table 4.

Table 4. Comparative Results Using All Three Test for Pet Rabbits

TABLE 4

Comparative Results Using All Three Test for Pet Rabbits

| | Positive/total samples tested (%) |
|---|---|
| Culture | 2/55 (3.64) |
| PCR | 11/38 (28.95) |
| Serology | 25/55 (45.45) |

In addition, the present inventors analyzed seven serum samples which had been tested at commercial laboratories for *P. multocida.* All animals which were positive by other tests were also positive in the neuraminidase ELISA. Table 5. Comparison of Present ELISA with Commercial Diagnostic Test Results

TABLE 5

Comparison of Present ELISA with Commercial Diagnostic Test Results

| | Rabbit | | | | | | |
|---|---|---|---|---|---|---|---|
| | 1 | 2 | 3 | 4 | 5 | 6 | 7 |
| Clinical signs | + | + | − | − | − | − | − |
| Other tests* | not done | not done | not done | +/− | + | +/− | + |
| ELISA | + (1:16) | + (1:128) | − | − | + (1:64) | − | + (1:16) |

*These samples were tested at a commercial laboratory by bacterial culture or whole cell ELISA.
Not done = no commercial testing performed;
+/− = test inconclusive.

Compositions and immunogenic preparations, including vaccine compositions, comprising substantially purified recombinant neuraminidase from *P. multocida* or an immunogenic peptide having an amino acid sequence derived therefrom capable of inducing protective immunity in a suitably treated mammal and a suitable carrier therefor are provided. Alternatively, hydrophilic regions of the neuraminidase can be identified by the skilled artisan, and peptide antigens can be synthesized and conjugated to a suitable carrier protein (e.g., bovine serum albumin or keyhole limpet hemocyanin) if needed for use in vaccines or in raising antibody specific for the exemplified neuraminidase. Immunogenic compositions are those which result in specific antibody production when injected into a human or an animal. Such immunogenic compositions or vaccines are useful, for example, in immunizing an animal, including humans, against infection and disease caused by *P. multocida*. The vaccine preparations comprise an immunogenic amount, of the exemplified neuraminidase or an immunogenic fragment(s) thereof. Such vaccines may comprise neuraminidase, or in combination with another protein or other immunogen or an epitopic peptide derived therefrom. By "immunogenic amount" is meant an amount capable of eliciting the production of antibodies directed against the exemplified neuraminidase in an individual or animal to which the vaccine has been administered.

Immunogenic carriers can be used to enhance the immunogenicity of the neuraminidase or peptides derived in sequence therefrom. Such carriers include but are not limited to proteins and polysaccharides, liposomes, and bacterial cells and membranes. Protein carriers may be joined to the neuraminidase or peptides derived therefrom to form fusion proteins by recombinant or synthetic means or by chemical coupling. Useful carriers and means of coupling such carriers to polypeptide antigens are known in the art.

Preferred fusion proteins which are effective for stimulating an immune response, especially when administered orally (e.g., in food or water) include those fusion with a cholera toxin fragment, or so-called LTB fusion. These methods are described in Dougan et al. (1990) *Biochem. Soc. Trans.* 18:746–748 and Elson et al. (1984) *J. Immunol.* 132:2736–2741.

The immunogenic compositions and/or vaccines may be formulated by any of the means known in the art. They are typically prepared as injectables, either as liquid solutions or suspensions. Solid forms suitable for solution in, or suspension in, liquid prior to injection may also be prepared. The preparation may also, for example, be emulsified, or the protein(s)/peptide(s) encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

Neuraminidase as exemplified herein and/or epitopic fragments or peptides of sequences. derived therefrom or from other *P. multocida* strains having primary structure similar (more than 90% identity) to the exemplified neuraminidase may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

Multiantigenic peptides having amino acid sequences derived from the exemplified NanH for use in immunogenic compositions are synthesized as described in Briand et al. (1992) *J. Immunol. Methods* 156:255–265. The sequences chosen are selected as being parts of "loops" predicted from structural studies of other neuraminidases. Sequences used include VVMFDLRWKTASDQNRIDPG (SEQ ID NO:1), MHGTWAAGTQNWYRDRLSY (SEQ ID NO:2) and HKHQVAIIRPGSGNAGAGYSSLAY (SEQ ID NO:3). Animals immunized with these peptides are immune to *P. multocida* disease, particularly when one or more booster immunizations are provided.

The immunogenic compositions or vaccines are administered in a manner compatible with the dosage formulation, and in such amount as will be prophylactically and/or therapeutically effective. The quantity to be administered, which is generally in the range of about 100 to 1,000 μg of protein per dose, more generally in the range of about 5 to 500 μg qf protein per dose, depends on the subject to be treated, the capacity of the individual's immune system to synthesize antibodies, and the degree of protection desired. Precise amounts of the active ingredient required to be administered may depend on the judgment of the veterinarian, physician or doctor of dental medicine and may be peculiar to each individual, but such a determination is within the skill of such a practitioner. Especially for poultry vaccinations where injection is not practical due to the number of birds to be treated, immunogenic compositions can be administered orally via food or water preparations comprising an effective amount of the protein(s) and/or peptide(s), and these immunogenic compositions may be formulated in liposomes as known to the art.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

All references cited herein are hereby incorporated by reference in their entirety to the extent that they are not inconsistent with the present disclosure.

Except as noted hereafter, standard techniques for peptide synthesis, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics,* Cold spring Harbor Laboratory, Cold Spring Harbor, N.Y., Old Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

The foregoing discussion and the following examples illustrate but are not intended to limit the invention. The skilled artisan will understand that alternative methods may be used to implement the invention.

EXAMPLE 1

Isolation and Characterization of nanH Sequences

A genomic library of *P. multocida* isolate R1913 (serotype A:3,4) was prepared by standard methods [Ausubel et al. (1993) *Current Protocols in Molecular Biology.* Greene Pub. Ass. Inc. & John Wiley & Sons Inc. Boston, Mass.] using Sau3A-digested genomic DNA and lambda ZAP cloning vector (Stratagene, La Jolla, Calif.). Recombinants were screened in *E. coli* for neuraminidase activity using 2'-(4-methylumbelliferyl)α-D-N-acetylneuraminic acid as substrate on filter paper as previously described [Moncla and Braham (1989) *J. Clin. Microbiol.* 27(1):182–184]. Positive clones were purified and analyzed further.

A 3.2 kb insert was subcloned and sequenced by dideoxy-termination using a combination of nested deletions and primer-walking at the Molecular Genetics Instrumentation Facility (University of Georgia). A 1.7 kb fragment was subcloned into the vector pQE32 (Qiagen, Chatsworth, Calif.) and the protein was isolated and purified as per the manufacturer's protocols. Protein gel electrophoresis (SDS-PAGE) was performed using standard methodology [Ausubel et al. (1993) *Current Protocols in Molecular Biology.* Greene Publishing Associates, Inc. & John Wiley & Sons Inc. Boston, Mass.]. Forward and reverse DNA sequence from each construct was confirmed by comparing sequence scans from MGIF. Alignment analysis was conducted using Gene Runner 3.04 (Hastings Software, N.Y.). The DNA sequences were then translated to amino acid sequences using Gene Runner 3.04, and these were also aligned using the GenBank sequences of the *S. typhimurium* and *C. perfringens* NanH. Gaps introduced into either the reference sequence or a query sequence to optimize alignment are treated as mismatches in calculations of percent sequence identity (or homology). Percent identity is calculated as [number of residues in query sequence−number of mismatches with reference sequence÷number of residues in reference sequence]×100%. Secondary peptide structure of the *P. multocida* neuraminidase was predicted using the algorithm of Garnier-Robson and hydropathy predictions by the algorithm of Goldman, Engelman, Steitz using the Gene Runner software.

EXAMPLE 2

DNA/DNA Hybridization

Chromosomal DNAs from *P. multocida* isolates were extracted from cell suspensions by the standard CTAB method described by Ausubel et al. (1993) *Current Protocols in Molecular Biology.* Greene Pub. Ass. Inc. & John Wiley & Sons Inc. Boston, Mass. Genomic DNA was digested with HindIII and size-separated on a 0.7% agarose gel. DNA was transferred and hybridized using the protocol for Southern blotting on nylon membranes according to Ausubel et al. (1993) *Current Protocols in Molecular Biology,* Greene Publishing & John Wiley & Sons Inc. Boston, Mass. High stringency washes were performed using 0.1×SSC containing 0.1% SDS at 68° C.; low stringency washes were performed at 55° C.

EXAMPLE 3

Synthesis of Multiantigenic Peptides

Multiantigenic peptides were synthesized using automated solid state peptide synthesis (Applied Biosystems, Foster City, Calif.) and a multi-lysine base according to Briand et al. (1992) *J. Immun. Methods* 156:255–265 and Posnett et al. (1988) *J. Biol. Chem.* 263:1719–1725. The multiple lysine base provides a framework for the simultaneous synthesis of multiple identical peptides and results in an "octopus"-like molecule which is antigenic without the need for conjugation to a carrier peptide. The multiple lysine base is not itself antigenic. Thus, this technique offers some advantages over the previous peptide immunizations which required conjugation to carrier proteins such as keyhole limpet hemocyanin and bovine serum albumin. Sequences of the three NanH-specific MAPs were VVMFDLRWKTASDQNRIDPG (SEQ ID NO:1), MHGTWAAGTQNWYRDRLSY (SEQ ID NO:2) and HKHQVAIIRPGSGNAGAGYSSLAY (SEQ ID NO:3). These peptides are formulated into compositions for administration to test animals for preparing NanH-specific antibody and protection assays using virulent *P. multocida* in challenge assays.

Unimmunized control animals are inoculated with only Freund's complete adjuvant. Test animals are immunized with 50 μg of MAP-peptides with Freund's complete adjuvant in the primary immunizations. Test animals are given booster immunizations of 50 μg MAP-peptide twice a week for 5 weeks in Freund's incomplete adjuvant.

EXAMPLE 4

Detection of nanH in Other Isolates of *P. multocida*

Forward primer 5'-GCTTTGAATGGCAGTTTATATGTG-3' (SEQ ID NO:6) and reverse primer 5'-TGAAGGAGCCGCTGTAGTCG-3' (SEQ ID NO:7) (derived from the *P. multocida* R1913 nanH gene) were used to amplify a fragment of 511 bp of the nanH, genes of nine field isolates of *P. multocida* isolated from fowl cholera outbreaks in Georgia and South Carolina and the Clemson University serotype 3×4 vaccine strain CU. All of these strains had been shown to express neuraminidase activity by the plate assay described by Moncla and Braham (1989) *J. Clin. Microbiol.* 27(1):182–184.

Oligonucleotide primers were synthesized by automated synthesis at the University of Georgia Molecular Genetics Instrumentation Facility. Samples were amplified through PCR with denaturation for 1 minute at 94° C., renaturation for 1 min at 55° C., and primer extension at 72° C. for 1 minute in a 30 cycle program using the Amplitron II thermocycler (Fisher Scientific, Pittsburgh, Pa.). The PCR amplification products were labeled according to the methods described by the nonradioactive Dig DNA labeling and detection kit (Boehringer Mannheim, Indianapolis, Ind.). The identity of the PCR products were confirmed by visual analysis using agarose gel electrophoresis and by DNA sequencing after purification of the PCR products from each isolate using the Magic DNA Clean-Up System (Promega, Madison, Wis.).

After nucleotide sequence determination for the amplification product for each isolate, sequences were aligned using the Gene Runner 3.04 software as above. The alignments were used to construct a phylogenetic tree using the PHYLIP algorithm. Secondary structure predictions were obtained using the algorithms of Garnier-Robson and Goldman, Engelman and Steitz using Gene Runner software.

DNA can be purified from biological samples such as infected tissue, respiratory system exudate, stool samples and mouse respiratory system and subjected to PCR amplification using the PCR primers disclosed hereinabove with subsequent sizing by agarose gel electrophoresis using appropriate agarose concentration, molecular weight markers and the CU or R1913 reference strains as positive control. The presence of virulent *P. multocida* is indicated by the generation of a 511 bp amplification product. Nucleotide sequence analysis of the amplification products and alignment of the sequence so obtained with a reference sequence such as that of the exemplified nanh sequence confirms the presence of a *P. multocida* neuraminidase coding sequence.

EXAMPLE 5

Neuraminidase Protection Data

Three week old leghorns (5 chickens per group) were immunized in the right pectoral muscle with oil bacterin containing: *P. multocida* serotype 1 (strain X-73) cells, MAPs 160, 161, 162 (100 μg) or PBS. Oil bacterin was prepared using protocol of Heddleston, and Rebers (1972) *Avian Diseases* 16:578–586. Chickens were challenged at 6 weeks of age with 3000 colony forming units (cfu) (in 100 μl PBS) of *P. multocida* strain X-73 injected in the left pectoral muscle (IM). 10 birds were in each group with 10 unvaccinated, unchallenged controls. The 5 birds immunized with PBS in oil died within 24 hours; 7/10 birds immunized with MAP160 died within 24 hours; 8/10 immunized with MAP161 died within 24 hours; 8/9 birds immunized with MAP162 died within 4 days. 5/5 birds vaccinated with *P. multocida* X-73 bacterin survived with no signs of illness. All of the MAP-immunized survivors had infections of the hockjoint and were lame. All of the unvaccinated, unchallenged controls were healthy at end of the experiment.

When three-week old leghorns were immunized with 100 μg of MAP 162 (in oil) followed at 5 weeks by 1 μg purified recombinant neuraminidase (in oil) (enzymatically active when purified) and then challenged at 6 weeks with 350 cfu of *P. multocida* X-73) IM; 4/4 chickens survived for 72 hours, at which time they were euthanized. 5/5 birds immunized with PBS in oil at 3 weeks and challenged at 6 weeks died; 5/5 birds vaccinated with *P. multocida* X-73 bacterin (using same protocol) survived. 5/5 birds received crude recombinant neuraminidase bacterin (40 μg protein/bird in which the neuraminidase is a minor component) at 3 and 15 weeks of age died within 24 hours. Desirably, animals vaccinated with *P. multocida* neuraminidase or antigenic peptides whose sequences are derived therefrom receive booster immunizations after the initial immunization.

EXAMPLE 6

Immunoassays

Immunoassays can be carried out using any known technology, with the substitution of *P. multocida* neuraminidase-specific antibody for the antibody specific to the previously exemplified target molecule. See, e.g., U.S. Pat. Nos. 4,916,056, 5,008,080, 5,418,136, 5,468,606, 5,482,830 and 5,550,063. The neuraminidase-specific antibody can be monoclonal or polyclonal, and if polyclonal, can be produced in any of a number of animals including, but not limited to, goats, rabbits and mice.

ELISA technology can also be applied to *P. multocida* neuraminidase-specific antibodies for detection or diagnosis of *P. multocida* in human or animal samples of biological samples including, but not limited to, serum, blood, saliva, tissue samples, lesion swabs, scrapings, and the like. In the example below, rabbit pasteurellosis was used as a model.

We have created a neuraminidase-based diagnostic test, an ELISA which uses patient serum or other patient samples, to detect *Pasteurella multocida* infection using rabbit pasteurellosis as a model. The test is an enzyme-linked immunosorbent assay is based on a modified method by Voler et al. (1976) *Bull. World Health Organization* 53:59–65. Recombinant neuraminidase protein which contains an amino-terminal histidine tag (6 histidine residues) was purified by affinity chromatography on a zinc column. 0.5 μg of recombinant protein in carbonate/bicarbonate buffer (pH 9.6) was used to coat the wells of ELISA plates. Rabbit sera, including pre-immune and post-immune control samples, were diluted twofold in conjugate buffer (PBS+0.1% Tween 20+5% nonfat dry milk) from 1:4 to a final dilution of 1:128. All determinations were done in duplicate. The presence of antibodies against *Pasteurella multocida* neuraminidase were detected with horseradish peroxidase-conjugated goat anti-rabbit antibody using O-phenylenediamine substrate. Quantitative measurements were made by determining absorbance at 490 nm using a microplate reader (Bio-Tek Instruments, Inc., Winooski, Vt.).

A positive reading (i.e., a positive result) occurs if the absorbance is greater than 4 standard deviations above the mean of the negative control serum [Muir, P. (1990) In: *ELISA in the Clinical Microbiology Laboratory,* Wreghitt T G, Morgan-Capner P. Eds. Published by the Public Health Laboratory Service (UK)]. We obtained serum from rabbits from a certified "Pasteurella-free" colony and based on these parameters the mean of our negative control serum was determined as 0.052, the standard deviation as 0.0256. Therefore, readings above 0.154 were considered positive, and readings below were considered negative. A test serum sample is considered positive if a positive reading is obtained at dilution 1:16 or above. Positive control serum was obtained by immunizing a rabbit with the recombinant neuraminidase protein in incomplete Freund's adjuvant. The pre-immunization serum from this rabbit was negative by our parameters, the post-immunization serum obtained had an IgG titer of 1:18,000.

Figure 5:
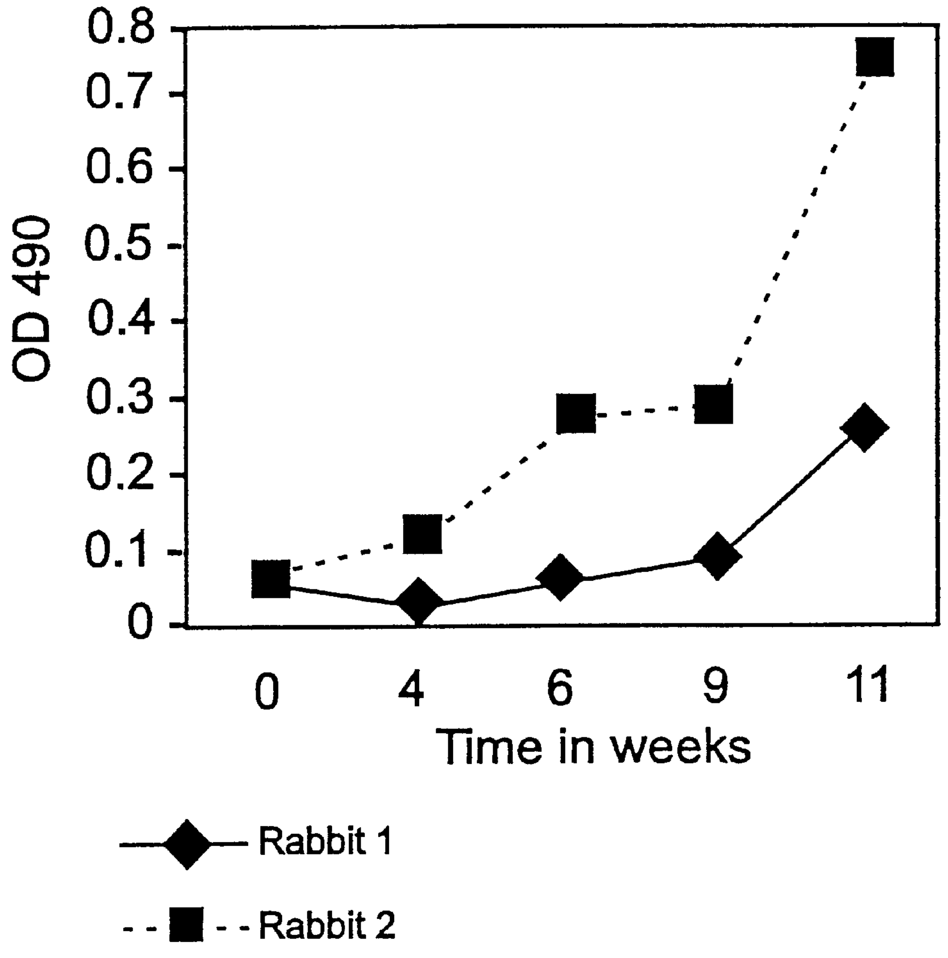
FIG. 5 graphically illustrates the increases in antibody titers over time in two rabbits challenged with *P. multocida.* Titers were measured using the ELISA described in Example 6 below. Animals were exposed to *P. multocida* at week 0. The titer is shown at a 1/16 dilution of serum. Using the parameters established with negative serum, a reading above 0.15 is positive.

In order to correlate the presence of anti-neuraminidase serum antibody with *Pasteurella multocida* infection, we exposed rabbits to the bacteria and monitored their seroconversion over time. Two rabbits were exposed to a mixture of 3 lapine isolates of *P. multocida* by placing a drop of bacterial culture in each nostril. Blood samples were removed weekly and tested in the ELISA. After 13 weeks, the animals were sacrificed, necropsied, and tissues cultured for the presence of *P. multocida.* While the animals did not demonstrate signs oft illness at any time during the course of the experiment, both animals demonstrated a rising titer of anti-neuraminidase antibody (FIG. 5). *Pasteurella multocida* was also cultured from the trachea of both animals at the end of the study, which confirms that they were colonized.

Free testing was offered to five veterinary practices specializing in exotic pets. Serum samples from rabbits suspected of having pasteurellosis were used to demonstrate the application of the test. Some submissions also included nasal or lesion swabs for culture. Swabs were placed in brain heart infusion broth which was used for culture and PCR detection of *P. multocida*. For the PCR we followed the method of Kasten et al. (1997) *Avian Diseases* 41:676–682. Fifty five serum samples and 38 swabs were obtained and tested.

TABLE 1

| PCR Products Sequenced and Aligned | |
|---|---|
| R1913 | GGGCGGCAGGAACACAAAACTGGTATCGAGACAGACTAAGCTATTTTAATCAGAATATTTGGGCG |
| CU | .............GA.C..........A..................................... |
| 162 | ................................................................. |
| 1796 | .........................C..C......A...A...C..................... |
| 2120 | ................................................................. |
| 241 | .........................C..C......A...A...C..................... |
| 2667 | .........................C..C......A...A...C..................... |
| 67-2 | .........................C..C......A...A...C..................... |
| 6796C | .........................C..C......A...A...C..................... |
| | |
| R1913 | GCAACAATTTATAAATCCACTGATGGTGGATTAAGTTGGCAAAAAAATACTGAATTCAGCAATAC |
| CU | ...............................................C................. |
| 162 | ................................................................. |
| 1796 | .......................C...................................T..... |
| 2120 | ................................................................. |
| 241 | .......................C...................................T..... |
| 2667 | .......................C...................................T..... |
| 67-2 | .......................C...................................T..... |
| 6796C | .......................C...................................T..... |
| | |
| R1913 | TGTGAATCGCGATGTTTTTATGAAAGTACAAAAAGGGGTAGGTAATCCCACAATTGGATTTTTAG |
| CU | ......................................C...............C.......... |
| 162 | ................................................................. |
| 1796 | .............A......................A.C.........A..C............. |
| 2120 | ................................................................. |
| 241 | .............A......................A.C.........A..C............. |
| 2667 | .............A......................A.C.........A..C............. |
| 67-2 | .............A......................A.C.........A..C............. |
| 6796C | .............A......................A.C.........A..C............. |
| | |
| R1913 | GCGGTGTGGGAACGGGAATTGTGATGAAAGACGGTACATTAGTTTTCCCAATCCAAACAGCACAT |
| CU | .................................................T............... |
| 162 | ................................................................. |
| 1796 | ................G..............T........G........G............... |
| 2120 | ................................................................. |
| 241 | ................G..............T........G........G............... |
| 2667 | ................G..............T........G........G............... |
| 67-2 | ................G..............T........G........G............... |
| 6796C | ................G..............T........G........G............... |
| | |
| R1913 | CGTGAAGGTATTGCCACGACAATTATGTATTCTAAAGATAATGGAAGAACCTGGGATATGCCGAC |
| CU | ..A.CT........T.................G.............A................G. |
| 162 | ................................................................. |
| 1796 | .....T........T.................G.............A................G. |
| 2120 | ................................................................. |
| 241 | .....T........T.................G.............A................G. |
| 2667 | .....T........T.................G.............A................G. |
| 67-2 | .....T........T.................G.............A................G. |
| 6796C | .....T.....C....................G...........C.A...T.....C.....AG. |
| | |
| R1913 | AATTAATAATGCGTTAGCACCGAATCCAAGCTCTTTAGAAAATATGGTATTCGAAATTGACAATA |
| CU | .......G....T.............A...T.................................. |
| 162 | ................................................................. |
| 1796 | .......G....T.................................................... |
| 2120 | ................................................................. |
| 241 | .......G....T.................................................... |
| 2667 | .......G....T.................................................... |
| 67-2 | .......G....T.................................................... |
| 6796C | .....................A....A...T...........C.....G................ |
| | |
| R1913 | AGTTAGTGATGACAGGGCGAGAAGATAATGGAAAAAAAACAAGGTGGGCGTATTACACTGAAGAT |
| CU | .............................A..C................................ |
| 162 | ................................................................. |
| 1796 | .............................A..C................................ |
| 2120 | ................................................................. |
| 241 | .............................A..C................................ |

TABLE 1-continued

| PCR Products Sequenced and Aligned | |
|---|---|
| 2667 | .............................A..C................................ |
| 67-2 | .............................A..C................................ |
| 6796C | .............................A..C................................ |
| | |
| R1913 | TTAGGGCAAACTTGGCATGTTTATGAACCA |
| CU | .....AA...........C........... |
| 162 | .............................. |
| 1796 | .............................. |
| 2120 | .............................. |
| 241 | .............................. |
| 2667 | .............................. |
| 67-2 | .............................. |
| 6796C | .....AA...........C........... |

R1913 is the reference sequence
Dots in other sequences are bases which are identical to those of the reference sequence.

The *P. multocida* strain R1913, 1562 and 2120 neuraminidase coding sequences are given in SEQ ID NO:4, nucleotides 651–1136. The partial sequence from the CU strain is given in SEQ ID NO:22, the partial sequences for strains 1796, 241, 2667 and 67-2 are given in SEQ ID NO:23, and the partial sequence for the 6796C strain neuraminidase is given in SEQ ID NO:24.

TABLE 2

DNA sequence translated and aligned

| N | | 11 | 21 | 31 | 41 | 51 |
|---|---|---|---|---|---|---|
| 1 | AAGTQNWYRD | RINYFNQNIW | AATIYKSTDG | GLSWQKNTEF | SNTVMRDIFM | KVQKGAGNPT |
| r1913.pir | .......... | .LS....... | .......... | .......... | .......V.. | .....V.... |
| cu.pir | ....N...Q. | .LS....... | .......... | .......... | .......V.. | .......... |
| 162.pir | .......... | .LS....... | .......... | .......... | .......V.. | .....V.... |
| 1796.pir | .......... | .......... | .......... | .......... | .......... | .......... |
| 2120.pir | .......... | .LS....... | .......... | .......... | .......V.. | .....V.... |
| 241.pir | .......... | .......... | .......... | .......... | .......... | .......... |
| 2667.pir | .......... | .......... | .......... | .......... | .......... | .......... |
| 67-2.pir | .......... | .......... | .......... | .......... | .......... | .......... |
| 6797.pir | .......... | .......... | .......... | .......... | .......... | .......... |
| | | | | | | |
| N | | 71 | 81 | 91 | 1 | 11 |
| 61 | IGFLGGVGTG | IVMKDGTLVF | PIQTAHRDGI | ATTIMYSKDN | GKTWDMPAIN | DALAPNPSSL |
| r1913.pir | .......... | .......... | .......E.. | .......... | .R.....T.. | N......... |
| cu.pir | .......... | .......... | .......A.. | .......... | .......... | ......Q... |
| 162.pir | .......... | .......... | .......E.. | .......... | .R.....T.. | N......... |
| 1796.pir | .......... | .......... | .......... | .......... | .......... | .......... |
| 2120.pir | .......... | .......... | .......E.. | .......... | .R.....T.. | N......... |
| 241.pir | .......... | .......... | .......... | .......... | .......... | .......... |
| 2667.pir | .......... | .......... | .......... | .......... | .......... | .......... |
| 67-2.pir | .......... | .......... | .......... | .......... | .......... | .......... |
| 6797.pir | .......... | .......... | .......... | .......... | .......... | N.....Q... |
| | | | | | | |
| N | | 31 | 41 | 51 | 61 | 71 |
| 121 | ENMVFEIDNK | LVMTGREDNR | QKTRWAYYTE | DLGQTWHVYE | P | |
| r1913.pir | .......... | .........G | K......... | .......... | . | |
| cu.pir | .......... | .......... | .......... | ...K...L.. | . | |
| 162.pir | .......... | .........G | K......... | .......... | . | |
| 1796.pir | .......... | .......... | .......... | .......... | . | |
| 2120.pir | .......... | .........G | K......... | .......... | . | |
| 241.pir | .......... | .......... | .......... | .......... | . | |
| 2667.pir | .......... | .......... | .......... | .......... | . | |
| 67-2.pir | .......... | .......... | .......... | .......... | . | |
| 6797.pir | .......... | .......... | .......... | ...K...L.. | . | |

The partial *P. multocida* sequences given above are as follows: reference, 241.pir, 2667.pir and 67-2.pir sequences are given in SEQ ID NO:25; R1913.pir, 162.pir, 2120.pir and 1796.pir sequences are given in SEQ ID NO:5, amino acids 135–295; cu.pir sequence is given in SEQ ID NO:26; and the 6797.pir sequence is given in SEQ ID NO:27.

Table 3

Reverse Sequence of PCR Products Aligned

Table 4

DNA Sequence Translated and Aligned

TABLE 3

Relatedness of nanH Homologues in *P. multocida* Isolates

| *P. multocida* strain or isolate | Serotype | % DNA Homology |
|---|---|---|
| R1913 | 3,4 | 100 |
| CU (Vaccine strain) | 3,4 | 95 |
| 162 | 3,4 | 100 |
| 2120 | 3,4 | 100 |
| 67-2 | 3,4 | 94.9 |
| 2667 | 3,4 | 94.9 |
| 1796 | 3,4 | 94.9 |
| 241 | 3,4 | 94.9 |
| 6797-C | 3 | 92.8 |
| X-73 | 1 | NA[a] |
| P-1059 | 3 | 99.6 |
| P-1662 | 4 | 90.1 |
| P-1702 | 5 | 90.3 |
| P-2192 | 6 | ND[b] |
| P-1997 | 7 | 95.5 |
| P-1581 | 8 | 93 |
| P-2095 | 9 | 92.8 |
| P-2100 | 10 | 97.5 |
| P-903 | 11 | 90.3 |
| P-1573 | 12 | 97.3 |
| P-1591 | 13 | 92.6 |
| P-2225 | 14 | NA |
| P-2237 | 15 | 90.1 |
| P-2723 | 16 | 93.4 |

[a]NA, no amplification product detected
[b]ND, not determined

What is claimed is:

1. An immunoassay kit for the diagnosis and/or detection of *Pasteurella multocida* in a biological sample from an animal or human, said immunoassay kit comprising a neuraminidase from *Pasteurella multocida,* and reagents for detection of specific binding of *Pasteurella multocida* neuraminidase to antibody in the biological sample, wherein the neuraminidase comprises the amino acid sequence as set forth in amino acids 1 to 412 of SEQ ID NO:5.

2. The immunoassay kit of claim 1 wherein the immunoassay is a radioimmunoassay, or an enzyme-linked, optical, fluorescence or particle-bound immunoassay.

3. The immunoassay kit of claim 1 wherein the neuraminidase comprises the amino acid sequence as set forth in amino acids 1 to 412 of SEQ ID NO:5 and further comprises an amino-terminal histidine tag.

4. A method for detecting *Pasteurella multocida* within an animal, said method comprising the steps of:

(a) obtaining at least one biological sample from an animal or human;

(b) reacting the sample of step (a) with the reagents and neuraminidase in the immunoassay kit of claim 1; and (c) detecting the presence or absence of specific binding of neuraminidase to antibody specific for *P. multocida* neuraminidase, within the sample, whereby *Pasteurella multocida* is detected when a specific binding is detected in step (c).

* * * * *

UNITED STATES PATENT AND TRADEMARK OFFICE

CERTIFICATE OF CORRECTION

PATENT NO. : 6,767,713 B2
DATED : July 27, 2004
INVENTOR(S) : Lee et al.

It is certified that error appears in the above-identified patent and that said Letters Patent is hereby corrected as shown below:

<u>Column 16,</u>
Line 10, delete the "."
Line 42, replace "qf" with -- of --

<u>Column 19,</u>
Line 65, replace "15" with -- 5 --

<u>Column 21,</u>
Line 1, replace "oft" with -- of --

<u>Column 25,</u>
Line 9, delete "Table 3"
Line 13, delete "Reverse Sequence of PCR Products Aligned"
Line 16, delete "Table 4"
Line 19, delete "DNA Sequence Translated and Aligned"

Signed and Sealed this

Twenty-eighth Day of December, 2004

JON W. DUDAS
*Director of the United States Patent and Trademark Office*

SEQUENCE LISTING

```
<160> NUMBER OF SEQ ID NOS:  27

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence:oligopeptide
      useful in immunogenic compositions

<400> SEQUENCE: 1

Val Val Met Phe Asp Leu Arg Trp Lys Thr Ala Ser Asp Gln Asn Arg
  1               5                  10                  15

Ile Asp Pro Gly
             20


<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence:oligopeptide
      useful in immunogenic compositions

<400> SEQUENCE: 2

Met His Gly Thr Trp Ala Ala Gly Thr Gln Asn Trp Tyr Arg Asp Arg
  1               5                  10                  15
```

-continued

```
Leu Ser Tyr


<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence:oligopeptide
      useful in immunogenic compositions

<400> SEQUENCE: 3

His Lys His Gln Val Ala Ile Ile Arg Pro Gly Ser Gly Asn Ala Gly
  1               5                  10                  15

Ala Gly Tyr Ser Ser Leu Ala Tyr
             20


<210> SEQ ID NO 4
<211> LENGTH: 2001
<212> TYPE: DNA
<213> ORGANISM: Pasteurella multocida
<220> FEATURE:
<221> NAME/KEY: CDS
<222> LOCATION: (188)..(1486)
<221> NAME/KEY: mat_peptide
<222> LOCATION: (251)..(1486)

<400> SEQUENCE: 4

caaaagctgg agctcgcgcg cctgcaggtc gacactagtg gatcttgctc catttttttgc     60

ttgactcatt tctaatatag ggtttatggg ggaatttttg aggggggttgt tttttattc    120

gatgtttata gacttgaaat taatcaattt tttacccta tacgaaaata atcctaagga    180

gaataaa atg aaa aag ccg gtg ttc ttg ttg tct tta ctc gca ctc tct      229
        Met Lys Lys Pro Val Phe Leu Leu Ser Leu Leu Ala Leu Ser
            -20                 -15                 -10

act tca atg gca gta cat ggt aac agc ttt tgg aaa gct gat ttg cat      277
Thr Ser Met Ala Val His Gly Asn Ser Phe Trp Lys Ala Asp Leu His
         -5              -1   1               5

gaa aat tta act aat gtg acg aaa agg gta ggc gtt gat ggt ttt act      325
Glu Asn Leu Thr Asn Val Thr Lys Arg Val Gly Val Asp Gly Phe Thr
 10                  15                  20                  25

gta aat aaa gaa ggt caa cct tgg cca ggg ata gga ccg aat ggc gaa      373
Val Asn Lys Glu Gly Gln Pro Trp Pro Gly Ile Gly Pro Asn Gly Glu
                 30                  35                  40

gcg ggt gga acc gtt aca ctg cct tat agc cgt att cca gct atg acg      421
Ala Gly Gly Thr Val Thr Leu Pro Tyr Ser Arg Ile Pro Ala Met Thr
             45                  50                  55

att aca gat gat aat aaa atg gtt gtg atg ttt gat tta cgg tgg aag      469
Ile Thr Asp Asp Asn Lys Met Val Val Met Phe Asp Leu Arg Trp Lys
         60                  65                  70

aca gca agt gac caa aat cgt atc gat cct ggc gcc gcg att tca gaa      517
Thr Ala Ser Asp Gln Asn Arg Ile Asp Pro Gly Ala Ala Ile Ser Glu
     75                  80                  85

gat ggg ggg cat agt tgg aaa aga att acc gct tgg aat ttt aat gat      565
Asp Gly Gly His Ser Trp Lys Arg Ile Thr Ala Trp Asn Phe Asn Asp
 90                  95                 100                 105

tca aaa att tct ttg cgt cgt gcg atg gac ccg aca tta ttg tac aac      613
Ser Lys Ile Ser Leu Arg Arg Ala Met Asp Pro Thr Leu Leu Tyr Asn
                110                 115                 120

agc att gat ggc agt tta tat gtg atg cac ggc act tgg gcg gca gga      661
Ser Ile Asp Gly Ser Leu Tyr Val Met His Gly Thr Trp Ala Ala Gly
            125                 130                 135

aca caa aac tgg tat cga gac aga cta agc tat ttt aat cag aat att      709
```

-continued

```
Thr Gln Asn Trp Tyr Arg Asp Arg Leu Ser Tyr Phe Asn Gln Asn Ile
        140                 145                 150

tgg gcg gca aca att tat aaa tcc act gat ggt gga tta agt tgg caa      757
Trp Ala Ala Thr Ile Tyr Lys Ser Thr Asp Gly Gly Leu Ser Trp Gln
    155                 160                 165

aaa aat act gaa ttc agc aat act gtg aat cgc gat gtt ttt atg aaa      805
Lys Asn Thr Glu Phe Ser Asn Thr Val Asn Arg Asp Val Phe Met Lys
170                 175                 180                 185

gta caa aaa ggg gta ggt aat ccc aca att gga ttt tta ggc ggt gtg      853
Val Gln Lys Gly Val Gly Asn Pro Thr Ile Gly Phe Leu Gly Gly Val
                190                 195                 200

gga acg gga att gtg atg aaa gac ggt aca tta gtt ttc cca atc caa      901
Gly Thr Gly Ile Val Met Lys Asp Gly Thr Leu Val Phe Pro Ile Gln
            205                 210                 215

aca gca cat cgt gaa ggt att gcc acg aca att atg tat tct aaa gat      949
Thr Ala His Arg Glu Gly Ile Ala Thr Thr Ile Met Tyr Ser Lys Asp
        220                 225                 230

aat gga aga acc tgg gat atg ccg aca att aat aat gcg tta gca ccg      997
Asn Gly Arg Thr Trp Asp Met Pro Thr Ile Asn Asn Ala Leu Ala Pro
    235                 240                 245

aat cca agc tct tta gaa aat atg gta ttc gaa att gac aat aag tta     1045
Asn Pro Ser Ser Leu Glu Asn Met Val Phe Glu Ile Asp Asn Lys Leu
250                 255                 260                 265

gtg atg aca ggg cga gaa gat aat gga aaa aaa aca agg tgg gcg tat     1093
Val Met Thr Gly Arg Glu Asp Asn Gly Lys Lys Thr Arg Trp Ala Tyr
                270                 275                 280

tac act gaa gat tta ggg caa act tgg cat gtt tat gaa cca gtt aat     1141
Tyr Thr Glu Asp Leu Gly Gln Thr Trp His Val Tyr Glu Pro Val Asn
            285                 290                 295

ggc ttt agt gcg act aca gcg gct cct tca caa ggt tca tcg att tat     1189
Gly Phe Ser Ala Thr Thr Ala Ala Pro Ser Gln Gly Ser Ser Ile Tyr
        300                 305                 310

gta acc tta ccg aat gga aaa cga ttt tta tta gtg tca aaa cca aat     1237
Val Thr Leu Pro Asn Gly Lys Arg Phe Leu Leu Val Ser Lys Pro Asn
    315                 320                 325

ggc aat ggc aat gat cgc tat gca aaa ggg aat ttg gca ctt tgg atg     1285
Gly Asn Gly Asn Asp Arg Tyr Ala Lys Gly Asn Leu Ala Leu Trp Met
330                 335                 340                 345

cta aat gca aaa aac cct aac cat aaa cat cag gta gca atc att aaa     1333
Leu Asn Ala Lys Asn Pro Asn His Lys His Gln Val Ala Ile Ile Lys
                350                 355                 360

ccg ggt tcg ggt aac agt gct ggt gca ggg tat tct cct tta gcc tat     1381
Pro Gly Ser Gly Asn Ser Ala Gly Ala Gly Tyr Ser Pro Leu Ala Tyr
            365                 370                 375

aaa aaa ggt aat tta ttt att gcc ttt gaa aac aat ggt gat att acc     1429
Lys Lys Gly Asn Leu Phe Ile Ala Phe Glu Asn Asn Gly Asp Ile Thr
        380                 385                 390

gtt aaa aat ctt agc gca cat atg caa gcg att gaa gaa aaa cca cag     1477
Val Lys Asn Leu Ser Ala His Met Gln Ala Ile Glu Glu Lys Pro Gln
    395                 400                 405

aat ggg gtt tgaccgatga aattgcgaca gaagtggaga aaatcaattc              1526
Asn Gly Val
410

gttagaacat ttaaataaag gacaaaaaga gacactaagc gccaaaatgc gccgagcgaa   1586

tgataatgcg gtggctgaat cgaacgtctt aaatcgagaa atgcatgaat taaaagacga   1646

agcaacatca cttgagcaaa aatcggtggc gatgagaaaa gcactgccct ctaaaatgaa   1706

acagtttaag cgagatcttg gagaagtacg tgatttaaca caactgacca atgaaaccta   1766
```

-continued ccttaattat cttggtatac aaggcttaat ggctatgtta aatgggtctt ttcttgcgct 1826 caatacgcca ttagattttt ctaagtacat aaaacaaggt gaaaagctca atagctatga 1886 cacggatatt ctttatagta cctataataa ggtgtttgtt gagtacgagt cagtgattaa 1946 aaacagccaa caccgtccga caattgcgct tggattaaat acaaggttac tgacc 2001

<210> SEQ ID NO 5
<211> LENGTH: 433
<212> TYPE: PRT
<213> ORGANISM: Pasteurella multocida

<400> SEQUENCE: 5

Met Lys Lys Pro Val Phe Leu Leu Ser Leu Leu Ala Leu Ser Thr Ser
    -20                 -15                 -10

Met Ala Val His Gly Asn Ser Phe Trp Lys Ala Asp Leu His Glu Asn
 -5              -1   1               5                  10

Leu Thr Asn Val Thr Lys Arg Val Gly Val Asp Gly Phe Thr Val Asn
             15                  20                  25

Lys Glu Gly Gln Pro Trp Pro Gly Ile Gly Pro Asn Gly Glu Ala Gly
         30                  35                  40

Gly Thr Val Thr Leu Pro Tyr Ser Arg Ile Pro Ala Met Thr Ile Thr
     45                  50                  55

Asp Asp Asn Lys Met Val Val Met Phe Asp Leu Arg Trp Lys Thr Ala
 60                  65                  70                  75

Ser Asp Gln Asn Arg Ile Asp Pro Gly Ala Ala Ile Ser Glu Asp Gly
                 80                  85                  90

Gly His Ser Trp Lys Arg Ile Thr Ala Trp Asn Phe Asn Asp Ser Lys
             95                 100                 105

Ile Ser Leu Arg Arg Ala Met Asp Pro Thr Leu Leu Tyr Asn Ser Ile
        110                 115                 120

Asp Gly Ser Leu Tyr Val Met His Gly Thr Trp Ala Ala Gly Thr Gln
    125                 130                 135

Asn Trp Tyr Arg Asp Arg Leu Ser Tyr Phe Asn Gln Asn Ile Trp Ala
140                 145                 150                 155

Ala Thr Ile Tyr Lys Ser Thr Asp Gly Gly Leu Ser Trp Gln Lys Asn
                160                 165                 170

Thr Glu Phe Ser Asn Thr Val Asn Arg Asp Val Phe Met Lys Val Gln
            175                 180                 185

Lys Gly Val Gly Asn Pro Thr Ile Gly Phe Leu Gly Gly Val Gly Thr
        190                 195                 200

Gly Ile Val Met Lys Asp Gly Thr Leu Val Phe Pro Ile Gln Thr Ala
    205                 210                 215

His Arg Glu Gly Ile Ala Thr Thr Ile Met Tyr Ser Lys Asp Asn Gly
220                 225                 230                 235

Arg Thr Trp Asp Met Pro Thr Ile Asn Asn Ala Leu Ala Pro Asn Pro
                240                 245                 250

Ser Ser Leu Glu Asn Met Val Phe Glu Ile Asp Asn Lys Leu Val Met
            255                 260                 265

Thr Gly Arg Glu Asp Asn Gly Lys Lys Thr Arg Trp Ala Tyr Tyr Thr
        270                 275                 280

Glu Asp Leu Gly Gln Thr Trp His Val Tyr Glu Pro Val Asn Gly Phe
    285                 290                 295

Ser Ala Thr Thr Ala Ala Pro Ser Gln Gly Ser Ser Ile Tyr Val Thr
300                 305                 310                 315

-continued

```
Leu Pro Asn Gly Lys Arg Phe Leu Leu Val Ser Lys Pro Asn Gly Asn
                320                 325                 330

Gly Asn Asp Arg Tyr Ala Lys Gly Asn Leu Ala Leu Trp Met Leu Asn
            335                 340                 345

Ala Lys Asn Pro Asn His Lys His Gln Val Ala Ile Ile Lys Pro Gly
        350                 355                 360

Ser Gly Asn Ser Ala Gly Ala Gly Tyr Ser Pro Leu Ala Tyr Lys Lys
    365                 370                 375

Gly Asn Leu Phe Ile Ala Phe Glu Asn Asn Gly Asp Ile Thr Val Lys
380                 385                 390                 395

Asn Leu Ser Ala His Met Gln Ala Ile Glu Glu Lys Pro Gln Asn Gly
                400                 405                 410

Val


<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 6

gctttgaatg gcagtttata tgtg                                          24


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      oligonucleotide useful as a primer

<400> SEQUENCE: 7

tgaaggagcc gctgtagtcg                                               20


<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:oligopeptide
      sequence

<400> SEQUENCE: 8

Phe Arg Ile Pro
  1


<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:consensus
      sequence for bacterial neuraminidases.
<221> NAME/KEY: VARIANT
<222> LOCATION: ()..)
<223> OTHER INFORMATION: Amino acid residues identified as Xaa are not
      specifically identified.

<400> SEQUENCE: 9

Ser Xaa Asp Xaa Gly Thr Trp
  1               5
```

-continued

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
oligonucleotide useful as a primer.

<400> SEQUENCE: 10
aagaccagat ctatgcatga aaatttaact 30

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:
oligonucleotide useful as a primer

<400> SEQUENCE: 11
agttttcgaa ttaaccccat tctgtg 26

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:peptide
motif in Pasteurella multocida neuraminidase

<400> SEQUENCE: 12

Ser Arg Ile Pro
1

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:portion of
Salmonella typhimurium neuraminidase

<400> SEQUENCE: 13

Ser Thr Asp Gly Gly Lys Thr Trp
1 5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:portion of
Salmonella typhimurium neuraminidase

<400> SEQUENCE: 14

Tyr Lys Ser Thr Asp Asp Gly Val Thr
1 5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:portion of
Salmonella typhimurium neuraminidase

<400> SEQUENCE: 15

Gly Gly Val Gly

-continued

1

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence:partial amino acid sequence of Salmonella typhimurium neuraminidase

<400> SEQUENCE: 16

Ser Phe Ile Tyr Ser Thr Asp Gly Ile Thr Trp Ser
1 5 10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:portion of Salmonella typhimurium neuraminidase

<400> SEQUENCE: 17

Thr Lys Asp Phe Gly Lys Thr Trp
1 5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:portion of Clostridium perfringens neuraminidase

<400> SEQUENCE: 18

Ser Thr Asp Phe Gly Lys Thr Trp
1 5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:partial amino acid sequence of Clostridium perfringens neuraminidase

<400> SEQUENCE: 19

Asn Gly Leu Thr Trp Ser Asn Lys Ile
1 5

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:portion of Clostridium perfringens neuraminidase

<400> SEQUENCE: 20

Leu Ile Ile Tyr Ser Lys Asp Asn Gly Glu Thr Trp
1 5 10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence:portion of -continued Clostridium perfringens neuraminidase

<400> SEQUENCE: 21

Ser His Asp Leu Gly Thr Thr Trp
1 5

<210> SEQ ID NO 22
<211> LENGTH: 485
<212> TYPE: DNA
<213> ORGANISM: Pasteurella multocida

<400> SEQUENCE: 22
gggcggcagg aacgaacaac tggtatcaag acagactaag ctattttaat cagaatattt 60
gggcggcaac aatttataaa tccactgatg gtggattaag ttggcaaaaa aacactgaat 120
tcagcaatac tgtgaatcgc gatgttttta tgaaagtaca aaaaggggca ggtaatccca 180
caatcggatt tttaggcggt gtgggaacgg gaattgtgat gaaagacggt acattagttt 240
tccctatcca aacagcacat cgagctggta ttgctacgac aattatgtat tcgaaagata 300
atggaaaaac ctgggatatg ccggcaatta atgatgcttt agcaccgaat caaagttctt 360
tagaaaatat ggtattcgaa attgacaata agttagtgat gacagggcga gaagataata 420
gacaaaaaac aaggtgggcg tattacactg aagatttagg aaaaacttgg catctttatg 480
aacca 485

<210> SEQ ID NO 23
<211> LENGTH: 491
<212> TYPE: DNA
<213> ORGANISM: Pasteurella multocida

<400> SEQUENCE: 23
gggcggcagg aacacaaaac tggtaccgcg acagaataaa ctatcttaat cagaatattt 60
gggcggcaac aatttataaa tccactgacg gtggattaag ttggcaaaaa aatactgaat 120
tcagtaatac tgtgaatcgc gatattttta tgaaagtaca aaaaggagca ggtaatccaa 180
ccattggatt tttaggcggt gtgggaacgg ggattgtgat gaaagatggt acattggttt 240
tcccgatcca aacagcacat cgagctggta ttgctacgac aattatgtat tcgaaagata 300
atggaaaaac ctgggatatg ccggcaatta atgatgcttt agcaccgaat ccaagctctt 360
tagaaaatat ggtattcgaa attgacaata agttagtgat gacagggcga gaagataata 420
gacaaaaaac aaggtgggcg tattacactg aagatttagg gcaaacttgg catgtttatg 480
aaccagttaa t 491

<210> SEQ ID NO 24
<211> LENGTH: 497
<212> TYPE: DNA
<213> ORGANISM: Pasteurella multocida

<400> SEQUENCE: 24
gggcggcagg aacacaaaac tggtaccgcg acagaataaa ctactttaat cagaatattt 60
gggcggcaac aatttataaa tccactgacg gtggattaag ttggcaaaaa aatactgaat 120
tcagtaatac tgtgaatcgc gatattttta tgaaagtaca aaaaggagca ggtaatccaa 180
ccattggatt tttaggcggt gtgggaacgg ggattgtgat gaaagatggt acattggttt 240
tcccgatcca aacagcacat cgtgatggta tcgccacgac aattatgtat tcgaaagata 300
atggcaaaac ttgggacatg ccagcaatta ataatgcgtt agcaccaaat caaagttctt 360

-continued

```
tagaaaacat ggtgttcgaa attgacaata agttagtgat gacagggcga gaagataata    420

gacaaaaaac aaggtgggcg tattagtgat gacagggcga gaagataatg gaaaaaaaac    480

aaggtgggcg tatcaac                                                   497


<210> SEQ ID NO 25
<211> LENGTH: 161
<212> TYPE: PRT
<213> ORGANISM: Pasteurella multocida

<400> SEQUENCE: 25

Ala Ala Gly Thr Gln Asn Trp Tyr Arg Asp Arg Ile Asn Tyr Phe Asn
  1               5                  10                  15

Gln Asn Ile Trp Ala Ala Thr Ile Tyr Lys Ser Thr Asp Gly Gly Leu
             20                  25                  30

Ser Trp Gln Lys Asn Thr Glu Phe Ser Asn Thr Val Asn Arg Asp Ile
         35                  40                  45

Phe Met Lys Val Gln Lys Gly Ala Gly Asn Pro Thr Ile Gly Phe Leu
     50                  55                  60

Gly Gly Val Gly Thr Gly Ile Val Met Lys Asp Gly Thr Leu Val Phe
 65                  70                  75                  80

Pro Ile Gln Thr Ala His Arg Asp Gly Ile Ala Thr Thr Ile Met Tyr
                 85                  90                  95

Ser Lys Asp Asn Gly Lys Thr Trp Asp Met Pro Ala Ile Asn Asp Ala
            100                 105                 110

Leu Ala Pro Asn Pro Ser Ser Leu Glu Asn Met Val Phe Glu Ile Asp
        115                 120                 125

Asn Lys Leu Val Met Thr Gly Arg Glu Asp Asn Arg Gln Lys Thr Arg
    130                 135                 140

Trp Ala Tyr Tyr Thr Glu Asp Leu Gly Gln Thr Trp His Val Tyr Glu
145                 150                 155                 160

Pro


<210> SEQ ID NO 26

<211> LENGTH: 161
<212> TYPE: PRT
<213> ORGANISM: Pasteurella multocida

<400> SEQUENCE: 26

Ala Ala Gly Thr Asn Asn Trp Tyr Gln Asp Arg Leu Ser Tyr Phe Asn
  1               5                  10                  15

Gln Asn Ile Trp Ala Ala Thr Ile Tyr Lys Ser Thr Asp Gly Gly Leu
             20                  25                  30

Ser Trp Gln Lys Asn Thr Glu Phe Ser Asn Thr Val Asn Arg Asp Val
         35                  40                  45

Phe Met Lys Val Gln Lys Gly Ala Gly Asn Pro Thr Ile Gly Phe Leu
     50                  55                  60

Gly Gly Val Gly Thr Gly Ile Val Met Lys Asp Gly Thr Leu Val Phe
 65                  70                  75                  80

Pro Ile Gln Thr Ala His Arg Ala Gly Ile Ala Thr Thr Ile Met Tyr
                 85                  90                  95

Ser Lys Asp Asn Gly Lys Thr Trp Asp Met Pro Ala Ile Asn Asp Ala
            100                 105                 110

Leu Ala Pro Asn Gln Ser Ser Leu Glu Asn Met Val Phe Glu Ile Asp
        115                 120                 125
```

-continued

```
Asn Lys Leu Val Met Thr Gly Arg Glu Asp Asn Arg Gln Lys Thr Arg
    130                 135                 140

Trp Ala Tyr Tyr Thr Glu Asp Leu Gly Lys Thr Trp His Leu Tyr Glu
145                 150                 155                 160

Pro


<210> SEQ ID NO 27
<211> LENGTH: 161
<212> TYPE: PRT
<213> ORGANISM: Pasteurella multocida

<400> SEQUENCE: 27

Ala Ala Gly Thr Gln Asn Trp Tyr Arg Asp Arg Ile Asn Tyr Phe Asn
  1               5                  10                  15

Gln Asn Ile Trp Ala Ala Thr Ile Tyr Lys Ser Thr Asp Gly Gly Leu
             20                  25                  30

Ser Trp Gln Lys Asn Thr Glu Phe Ser Asn Thr Val Asn Arg Asp Ile
         35                  40                  45

Phe Met Lys Val Gln Lys Gly Ala Gly Asn Pro Thr Ile Gly Phe Leu
     50                  55                  60

Gly Gly Val Gly Thr Gly Ile Val Met Lys Asp Gly Thr Leu Val Phe
 65                  70                  75                  80

Pro Ile Gln Thr Ala His Arg Asp Gly Ile Ala Thr Thr Ile Met Tyr
                 85                  90                  95

Ser Lys Asp Asn Gly Lys Thr Trp Asp Met Pro Ala Ile Asn Asn Ala
            100                 105                 110

Leu Ala Pro Asn Gln Ser Ser Leu Glu Asn Met Val Phe Glu Ile Asp
        115                 120                 125

Asn Lys Leu Val Met Thr Gly Arg Glu Asp Asn Arg Gln Lys Thr Arg
    130                 135                 140

Trp Ala Tyr Tyr Thr Glu Asp Leu Gly Lys Thr Trp His Leu Tyr Glu
145                 150                 155                 160

Pro
```